US011484678B2

(12) United States Patent
Frerichs et al.

(10) Patent No.: US 11,484,678 B2
(45) Date of Patent: Nov. 1, 2022

(54) BREATHING MASK WITH COUPLING ELEMENTS FOR HEAD STRAP

(71) Applicant: Loewenstein Medical Technology S.A., Luxembourg (LU)

(72) Inventors: Arnold Frerichs, Buxtehude (DE); Martin Bechtel, Winsen/Luhe (DE); Martin Eifler, Glueckstadt (DE); Joachim Gardein, Icod de los Vinos (ES)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 755 days.

(21) Appl. No.: 16/008,266

(22) Filed: Jun. 14, 2018

(65) Prior Publication Data
US 2018/0361101 A1    Dec. 20, 2018

(30) Foreign Application Priority Data

Jun. 19, 2017   (DE) .......................... 102017005691.9
Jun. 19, 2017   (DE) .......................... 102017005692.7
Jun. 19, 2017   (DE) .......................... 102017005693.5
Jun. 19, 2017   (DE) .......................... 102017005694.3
Jun. 19, 2017   (DE) .......................... 102017005703.6
Jun. 19, 2017   (DE) .......................... 102017005704.4

(51) Int. Cl.
*A61M 16/06*   (2006.01)
*A61M 16/08*   (2006.01)

(52) U.S. Cl.
CPC ........ *A61M 16/0816* (2013.01); *A61M 16/06* (2013.01); *A61M 16/0605* (2014.02);
(Continued)

(58) Field of Classification Search
CPC ................ A61M 16/06–0655; A61M 16/0683
See application file for complete search history.

(56) References Cited

U.S. PATENT DOCUMENTS 3,441,020 A * 4/1969 Aasen ............... A61M 16/0683
                                                       128/205.25
5,853,002 A * 12/1998 Kawasaki ............. A61M 11/06
                                                       128/200.14
(Continued)

FOREIGN PATENT DOCUMENTS

DE   102005041716 A1   4/2006
DE   102005041717 A1   4/2006
EP       1632262 B1    6/2016

OTHER PUBLICATIONS https://www.vocabulary.com/dictionary/funnel (last accessed Mar. 4, 2022).*

*Primary Examiner* — LaToya M Louis
(74) *Attorney, Agent, or Firm* — Abel Schillinger, LLP

(57) ABSTRACT

The invention relates to a respiratory mask of modular construction. The main components are reduced to four parts and are provided by the mask body, the forehead support, the mask bead and the attachment piece. The design, according to the invention, of the outflow structure between mask body and forehead support makes apertures in the mask body unnecessary for this purpose. The strap coupling in the region of the mask body is made easier by a funnel-shaped guide structure such that it is possible in a simple manner even without seeing it.

19 Claims, 25 Drawing Sheets

(52) U.S. Cl.
CPC .... *A61M 16/0611* (2014.02); *A61M 16/0633* (2014.02); *A61M 16/0638* (2014.02); *A61M 16/0825* (2014.02); *A61M 16/0683* (2013.01); *A61M 2205/582* (2013.01); *A61M 2205/583* (2013.01); *A61M 2209/082* (2013.01); *A61M 2209/088* (2013.01)

(56) References Cited

U.S. PATENT DOCUMENTS

| | | | | |
|---|---|---|---|---|
| 7,931,025 | B2* | 4/2011 | Eaton | A61M 16/06 128/202.27 |
| 8,042,542 | B2* | 10/2011 | Ging | A44B 11/266 128/200.24 |
| 8,051,855 | B2* | 11/2011 | Ho | A61M 16/06 128/206.21 |
| 8,783,253 | B2* | 7/2014 | Flaherty | A41D 13/1138 128/206.13 |
| 9,616,190 | B2* | 4/2017 | Rummery | A61M 16/00 |
| 9,950,131 | B2* | 4/2018 | Ng | A61M 16/06 |
| 9,981,102 | B2* | 5/2018 | Veliss | A61M 16/0683 |
| 9,987,451 | B2* | 6/2018 | Stegman | A61M 16/06 |
| 10,034,994 | B2* | 7/2018 | McAuley | A61M 16/024 |
| 10,118,009 | B2* | 11/2018 | Darkin | A61M 16/06 |
| 10,500,363 | B2* | 12/2019 | Raje | A61M 16/0638 |
| 2008/0210241 | A1 | 9/2008 | Schulz | |
| 2008/0230066 | A1* | 9/2008 | Chandaria | A41D 13/11 128/206.13 |
| 2008/0230068 | A1* | 9/2008 | Rudolph | A61M 16/06 128/206.28 |
| 2009/0126739 | A1* | 5/2009 | Ng | A61M 16/06 128/205.25 |
| 2011/0265796 | A1* | 11/2011 | Amarasinghe | A61M 16/06 128/206.28 |
| 2012/0204869 | A1* | 8/2012 | Gunaratnam | A61M 16/06 128/202.27 |
| 2012/0204870 | A1* | 8/2012 | McAuley | A61M 16/0616 128/203.12 |
| 2013/0228173 | A1* | 9/2013 | Busch | A61M 16/0683 128/202.27 |
| 2013/0284178 | A1* | 10/2013 | Eaton | A61M 16/06 128/205.25 |
| 2014/0083431 | A1* | 3/2014 | Burz | A61M 16/06 128/206.24 |
| 2014/0166018 | A1* | 6/2014 | Dravitzki | A61M 16/0875 128/207.13 |
| 2014/0202463 | A1* | 7/2014 | Ging | A61M 16/0875 128/205.25 |
| 2014/0305433 | A1* | 10/2014 | Rothermel | A61M 16/06 128/202.27 |
| 2015/0352308 | A1* | 12/2015 | Cullen | A61M 16/0683 128/205.25 |
| 2016/0279371 | A1* | 9/2016 | Dravitzki | A61M 16/0616 |
| 2016/0367778 | A1* | 12/2016 | Eves | A61M 16/0816 |
| 2017/0080173 | A1* | 3/2017 | Barlow | A61M 16/0816 |
| 2017/0128687 | A1* | 5/2017 | Price | A61M 16/0622 |
| 2017/0274168 | A1* | 9/2017 | Kwok | A61M 16/0638 |
| 2017/0333657 | A1* | 11/2017 | Stephenson | A61M 16/0825 |
| 2018/0001046 | A1* | 1/2018 | Rummery | A61M 16/0611 |
| 2018/0021536 | A1* | 1/2018 | Ng | A61M 16/06 128/206.24 |
| 2018/0043127 | A1* | 2/2018 | Matula, Jr. | A61M 16/065 |
| 2018/0361096 | A1* | 12/2018 | Grashow | A61M 16/0683 |

* cited by examiner

BREATHING MASK WITH COUPLING ELEMENTS FOR HEAD STRAP

CROSS-REFERENCE TO RELATED APPLICATIONS

The present application claims priority under 35 U.S.C. § 119 of German Patent Application Nos. 102017005691.9, 102017005692.7, 102017005693.5, 102017005694.3, 102017005703.6, 102017005704.4, and 102017005705.2, all filed on Jun. 19, 2017. The entire disclosures of these applications are expressly incorporated by reference herein.

BACKGROUND OF THE INVENTION

1. Field of the Invention

The invention relates to a respiratory mask with a mask body, and with a hinged attachment piece which is connectable to a breathing tube.

2. Discussion of Background Information

Respiratory masks are used, for example in connection with ventilators, to convey respiratory gas to the patient and to assist the discharge of the exhaled respiratory gas. The respiratory mask is typically connected to a ventilator via a breathing tube.

A disadvantage of known respiratory masks is the acoustic disturbance which resulted from the exhalation through the mask body and the breathing tube and which was unpleasant for the patient and the environment. Moreover, the exhaled stream of air gave rise to a cold draft brushing along the patient. These challenges were overcome by an adaptation of the mask according to DE 10 2005 041 717 A1 and EP 1 632 262 B1 by means of a suitable arrangement and structure of exhalation gaps between mask body and securing ring.

A disadvantage from the point of view of manufacture and maintenance is that the air in the known respiratory masks is guided to the exhalation gaps through apertures in the mask body. Moreover, apertures weaken the mechanical stability of the mask body.

Furthermore, the masks are composed of many individual parts which, although permitting increased adaptability to the patient, are complex to assemble and costly to manufacture.

In known masks, the space for receiving the respiratory openings of the patient is made available mainly inside the mask body. This entails an increased need for material in the region of the mask body, since the latter has to enclose a larger volume.

Moreover, in known respiratory masks, the coupling of the harness, for the purpose of securely fixing the mask on the head of the patient during fitting of the mask, often places high demands on the dexterity of the patient, since a view of the corresponding connection parts is not afforded.

SUMMARY OF THE INVENTION

An object of the invention is to make available a simple coupling of the harness.

The object is achieved by a respiratory mask with a mask bead, which seals off the mask in the direction of the patient, a mask body, and at least one wing which serves to receive a harness clip, wherein the harness clip fixes a head harness on the mask, characterized in that the wing has a funnel-shaped cutout, and the clip locks in the region of a locking point of the cutout.

The invention is characterized in that the cutout has two regions that are funnel-shaped to different extents.

The invention is characterized in that the locking point is arranged in the narrowest region of the funnel-shaped cutout.

The invention is characterized in that the mask body has, in the region of the wing, a spring plate which is arranged adjacent to and/or inside the cutout.

The invention is characterized in that the spring plate leans at least partially on the mask bead.

The invention is characterized in that the mask body has guide structures which direct the patient to the cutout and the joining direction of the clips.

The invention is characterized in that the guide structures are arranged on the base of the spring plate.

The invention is characterized in that the funnel guides the clip automatically to the locking point, in which the clip is fixed by the spring plate.

The invention is characterized in that the clip slides over the spring plate when it is guided to the locking point.

The invention is also characterized by a locking pin (20) on the side of the spring plate (18) facing toward the wing (12), which locking pin (20) permits the locking engagement of the harness clip (6).

The invention is also characterized by a respiratory mask having a forehead support (2).

The invention is also characterized by a respiratory mask having two different mechanical auxiliary structures for coupling of straps.

The invention is also characterized by a respiratory mask of which the forehead support (2), by virtue of its structure, has at least two options for the coupling of straps.

The invention is also characterized by a respiratory mask of which the strap coupling is embodied by at least one clip (6).

The invention is also characterized by a respiratory mask of which the mechanical auxiliary structure for the strap coupling is provided by a funnel-shaped structure (19) in the mask body (1).

The respiratory mask is also characterized in that the clip (6) has, on its upper face and lower face, depressions or elevations which are occupied by knobs or ribs (35), and, at one end, it has an eyelet (36) through which a retaining strap can be pulled and thus secured.

The invention is characterized in that the clip (6) has a pin (37) with a mushroom-shaped undercut.

The invention is characterized in that the clip (6) has a pin (37) with a mushroom-shaped undercut and has a depression (38), configured as a socket, in the head of the pin (37).

The invention is characterized in that the depression, in interaction with the locking pin on the spring plate of the mask body, ensures the locking engagement of the harness clip in the intended position on the wing of the mask body.

The invention is characterized in that the depression (38)/the locking pin (20) are axially centered in the axial direction of the pin (37).

The invention is characterized in that the depression (38) and/or the locking pin (20) are axially uncentered in the axial direction of the pin (37), wherein a pivoting movement of the clip about the axis of the pin (37) then leads to release of the connection between depression (38) and locking pin (20).

An object of the invention is to adapt the guide structures for the exhaled respiratory gases to the exhalation gaps such that no apertures are needed in the mask body.

According to the invention, this object is achieved by the fact that the guide structures are formed in the space which is created by cutouts between the mask body and a forehead support connector.

A further object of the invention is to reduce the number of individual parts needed, in order to permit cost-effective manufacture and simple assembly of the respiratory mask.

According to the invention, this object is achieved by the fact that the forehead support according to the invention combines several functions. Thus, the functions of the forehead support, the securing ring and the ball joint for receiving an attachment piece are combined in a single part. In addition, the contour of the forehead support, together with the mask body, defines a guide structure for the exhaled respiratory gases of a patient.

The assembly of the respiratory mask can additionally be simplified by the fact that the mask body is configured with rotational symmetry, as a result of which the mask body can be installed with an identical function in two positions at 180° with respect to each other.

A further object of the invention is to save material and reduce the manufacturing cost of the mask body.

This object is achieved by the fact that the space required at the respiratory openings of the patient is made available inside the mask bead.

Moreover, it is an object of the invention to make the strap coupling to the respiratory mask easier.

According to the invention, this object is achieved by adaptation of the mechanical construction of the strap coupling in such a way that a guide structure is integrated in the mask body, which guide structure assists in guiding the coupling structure present on the strap side to the fixing point during the coupling procedure. In this way, the coupling procedure is made considerably easier without seeing it.

Furthermore, this object is achieved by the fact that the forehead support affords different options for the strap coupling.

The respiratory mask according to the invention, which is to be understood not only as an individual part but also as an element of a complete ventilator, is preferably of a modular construction. This modularity comprises four main components, namely a mask body, a forehead support, a mask bead and a hinged attachment piece. The attachment piece is connectable to a breathing tube which transports the respiratory gas between respiratory mask and ventilator.

Moreover, the respiratory mask according to the invention is distinguished by the integration of at least one exhalation gap, which is delimited by certain regions of the surfaces of mask body and forehead support. To fix the respiratory mask to the head of a patient, straps are provided, for which the respiratory mask according to the invention provides coupling structures.

The mask body serves as a base of the respiratory mask and provides connection structures to the forehead support, to the mask bead and to the harness. The connection structures to mask bead and forehead support are preferably mechanically coded in order to ensure a defined positioning of the elements with respect to one another. The connection of mask body and forehead support is conceived in particular in the form of a bayonet catch with a locking function. The connection of mask body and mask bead can be realized, for example, by a plug connection with an undercut or by two-component adhesive bonding.

An advantageous embodiment of the mask body is for the latter to be designed with rotational symmetry. Thus, the mask body can be installed with an identical function in the respiratory mask in two positions offset by 180° to each other. However, for example for the purpose of mechanical coding or the configuration of exhalation gaps, mask bodies that are not completely rotationally symmetrical are also conceivable for a respiratory mask according to the invention.

At its sides, the mask body has coupling structures for straps. These are conceived in particular as the combination of a guide structure, which guides the mating piece on the strap side to the fixing point, and of a fixing mechanism. According to the invention, the fixing mechanism can be configured, for example, as a spring plate with a stub, while a funnel-shaped guide structure guides the strap-side coupling piece to the locking point defined by spring plate and stub.

The basic shape of the inner surface of the mask body is annular, for example, and opens out in a funnel shape on the side directed away from a patient. Furthermore, the surface in the inner radius of the mask body has structures which serve to mechanically secure the connection to the forehead support and to delimit one or more respiratory gas gas guide structures and at least one exhalation gap. These structures can be provided, for example, by spacer ribs, which permit a connection of mask body and forehead support without play and delimit the exhalation gaps. Furthermore, structures are provided which permit a secure connection and fixing of mask body and forehead support. They are conceived in particular as channel-like cutouts in a direction orthogonal to the radial plane, which serve as guides for bayonet teeth on the connection piece of the forehead support. Furthermore, in an advantageous embodiment of the respiratory mask according to the invention, the channels, which become free after mask body and forehead support have been screwed together, serve to guide the exhaled respiratory gases of a patient from the interior of the respiratory mask to the funnel.

The funnel-shaped opening makes it possible for the exhaled respiratory gases of a patient to be led away from the respiratory mask at an advantageous angle through at least one exhalation gap on the side directed away from the patient.

A configuration within the funnel-shaped opening of the mask body is advantageously provided which automatically closes the exhalation gaps in defined regions in connection with the mounted forehead support. For example, this concerns the region in which exhaled gases can escape directly in the direction of the eyes or are deflected by parts of the respiratory mask in the direction of the eyes, since this is particularly uncomfortable for patients.

However, embodiments are also possible which have at least one exhalation gap in the upwardly directed region of the funnel. Moreover, embodiments of the respiratory mask according to the invention can additionally use the further structure of the forehead support, particularly in the region of the web, as a guiding surface for the escaping respiratory gas.

The mask bead serves to receive the respiratory openings and to seal the mask on the face of a patient. The mask bead can be produced from a relatively soft material which, for the purpose of providing a seal on the face of a patient and for mounting on the mask body, can have a certain elasticity. In particular, the material conceived for the mask bead is plastic. The basic shape of the mask bead is preferably adapted to the human anatomy and is suitably triangular for nasal masks. On the side directed away from the patient, there is a connection opening which is adapted in size and shape to the connection form of the mask body. Through the combination of different shapes with further adapted circumferences of mask bead and mask body, the stiffness and the ratio of width and height can be adjusted in the relatively soft material of the mask bead. For example, an oval configuration of the bead seat on the mask body and a circular configuration of the opening on the mask bead are conceivable.

The forehead support of the respiratory mask according to the invention is configured in one piece and combines further functions. These functions are the completion of the guide structure for the exhaled respiratory gases of a patient in combination with the features provided in the mask body, in particular the funnel-shaped admission line of the respiratory gases to the at least one attachment piece, for example through an integrated ball cage, and also a strap coupling.

BRIEF DESCRIPTION OF THE DRAWINGS

The invention is explained below on the basis of exemplary embodiments and with reference to the figures, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
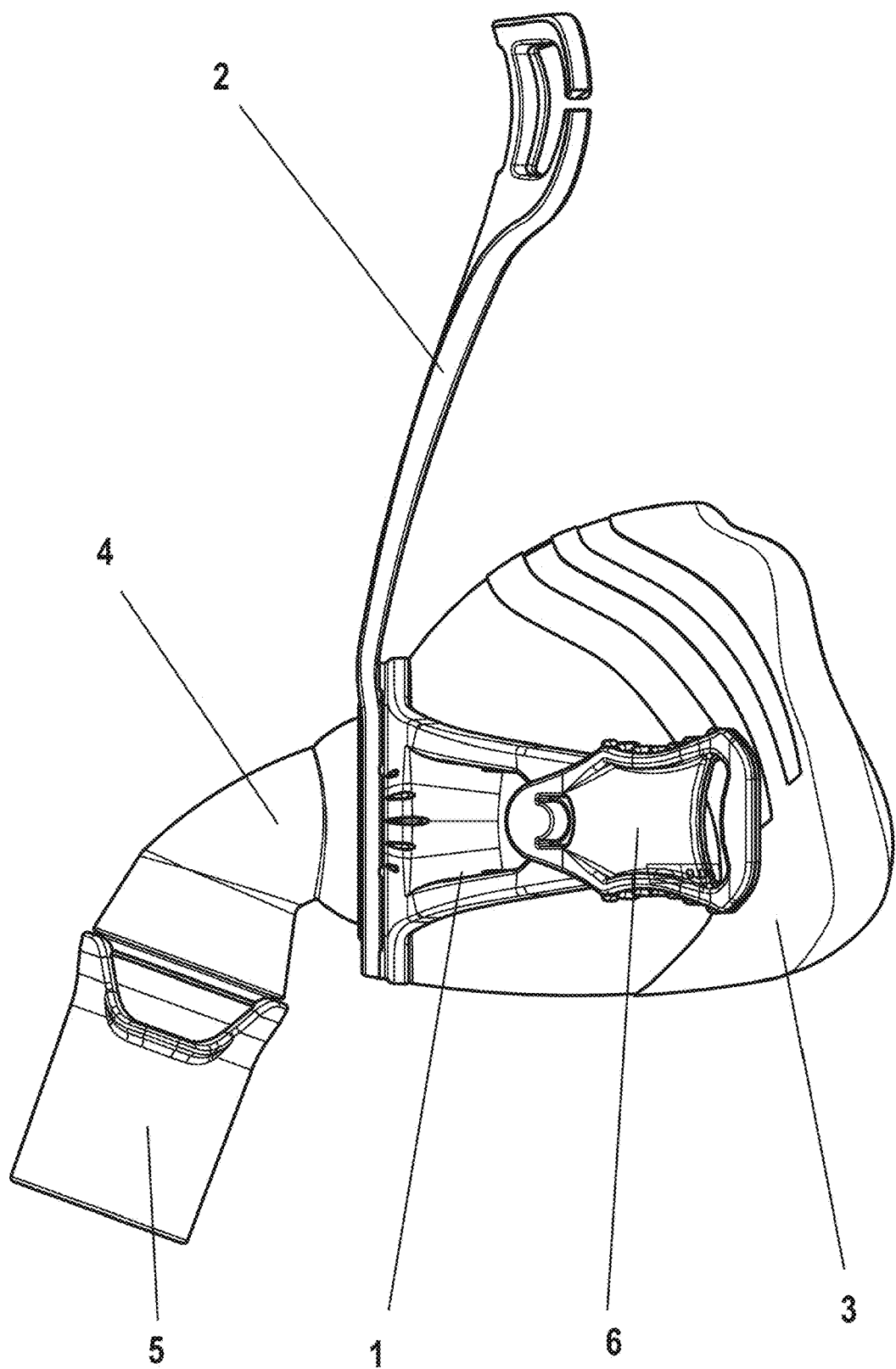
FIG. 1 shows a side view of a respiratory mask configured as a nasal mask.

FIG. 1 shows a respiratory mask configured as a nasal mask. The respiratory mask according to the invention is of modular construction. The mask body (1) serves as a base of the respiratory mask. This mask body (1) is configured, for example, as an injection-molded plastic part and is relatively firm. The mask body (1) is adjoined by the forehead support (2), which ensures a secure fit of the mask on the face of a patient (not shown), and by the mask bead (3) which, by virtue of its interference fit and its elastic nature, ensures a tight seal of the respiratory mask on the patient. The attachment piece (4) represents the connection to a tube (not shown) through which the respiratory gas is transported from a breathing apparatus to the respiratory mask. The tube is connected to the attachment piece (4) by means of a sleeve (5) mounted rotatably on the attachment piece (4). With the aid of clips (6), which are laterally connectable to the mask body (1), the respiratory mask can be securely fixed to the head of the patient by straps.

Figure 2:
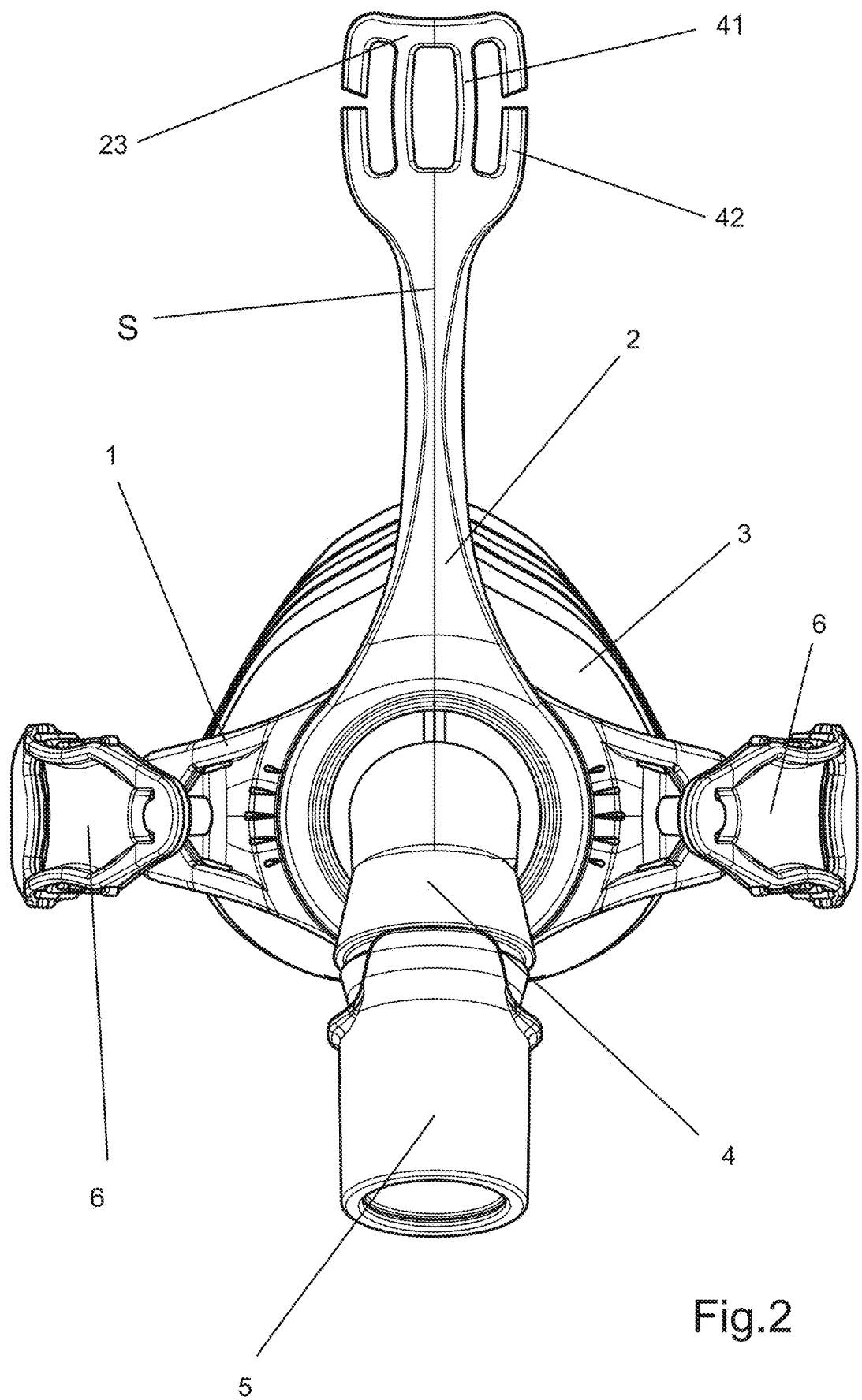
FIG. 2 shows a front view of the respiratory mask shown in FIG. 1.

FIG. 2 shows a front view of the embodiment of a respiratory mask according to the invention already shown in FIG. 1. The symmetry of the construction along the vertical center axis can be seen. A clip (6) for receiving a strap is located here on each side of the mask body (1), although an asymmetrical embodiment is also conceivable. The latter can be obtained, for example, if the connection between respiratory mask and securing strap is realized on one side by a clip (6), whereas a loop and a hook are used on the other side.

Figure 3:
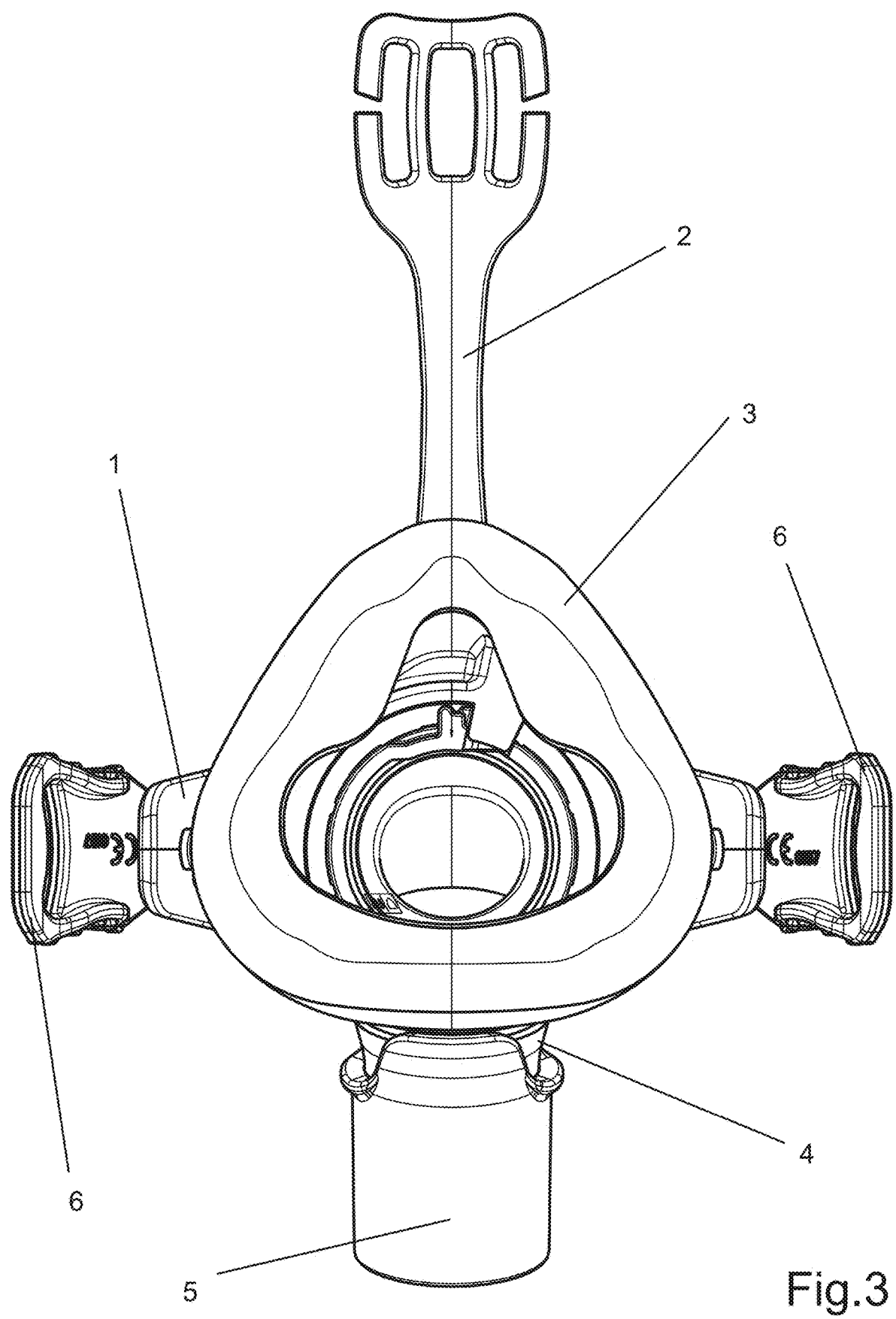
FIG. 3 shows a rear view of the respiratory mask shown in FIG. 1.

FIG. 3 shows a rear view of the respiratory mask from FIG. 1. It reveals a triangular basic shape of the mask bead (3) and also the interior of the respiratory mask through the patient-side opening of the mask bead (3). The forehead support (2) protrudes from the upper side of the mask bead (3). The clips (6) connected to the mask body (1) and used for coupling the strap can be seen at the sides of the respiratory mask. The attachment piece (4) with the mounted sleeve (5) protrudes from the underside of the mask bead (3). The clips protrude from the mask body in the direction of the patient. The clips thus form a continuation of the mask body (1) in the direction of the patient. This has the result that the engagement points for the harness are shifted closer to the ears of the patient.

Figure 4:
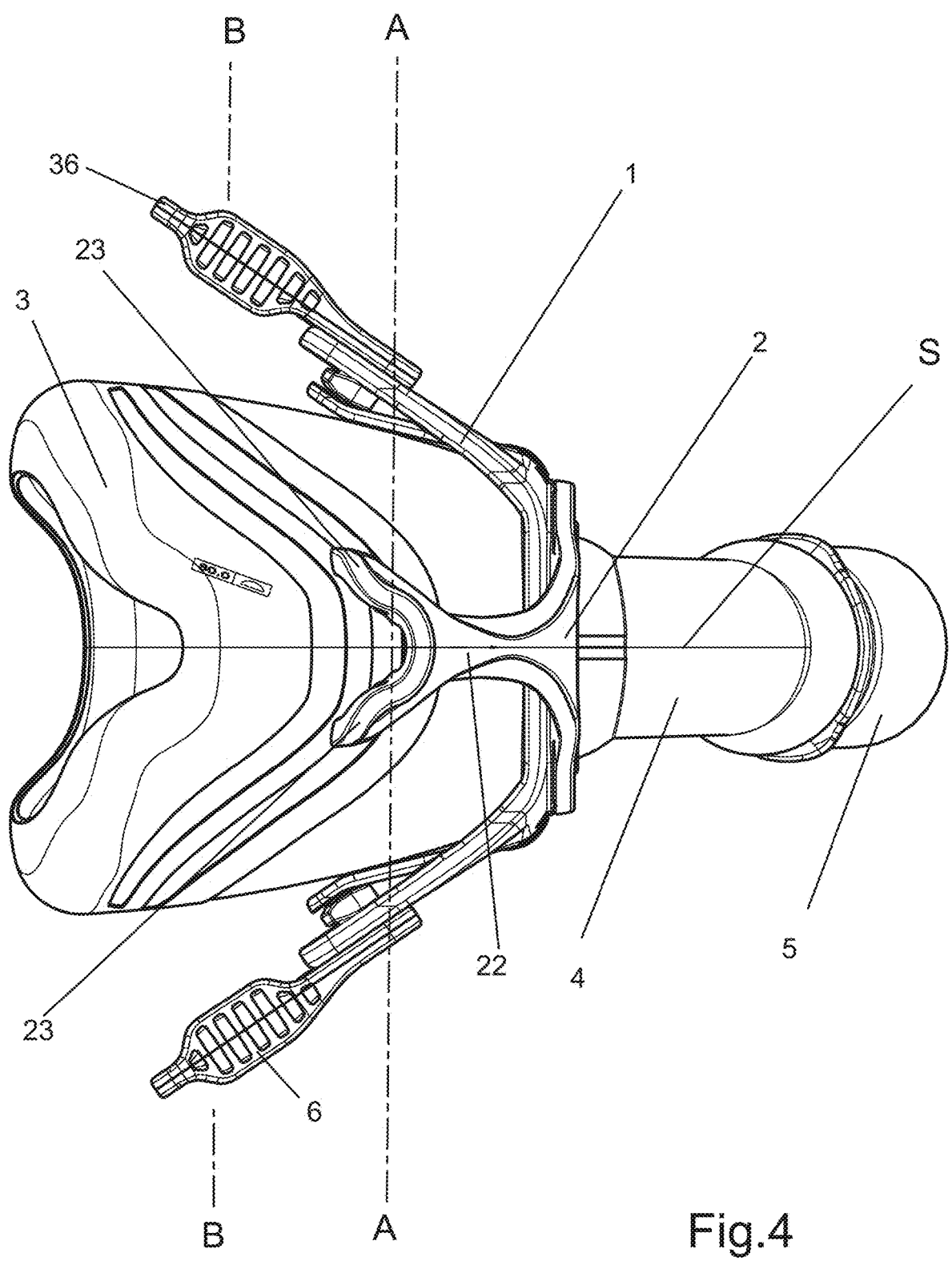
FIG. 4 shows a top view of the respiratory mask shown in FIG. 1.

FIG. 4 shows a top view of the respiratory mask from FIG. 1. This view reveals a configuration of the forehead support (2) adapted to the human anatomy. From the surface resulting from the connection to the mask body (1), the head end of the forehead support (2) protrudes in the direction of a patient in order to achieve a sufficient supporting function on the forehead of a patient without excessive inclination of the whole respiratory mask. The figure indicates the position of the eyelet (36), which serves for coupling the harness to the clip. It also reveals the strap coupling in the region of the forehead support (23). Through the symmetrical structure relative to the plane of symmetry S, the eyelets (36) and the strap coupling (23) are present on both sides. A plane A extends through both strap couplings (23) (and substantially parallel to the forehead of a patient). A plane B extends through both eyelets (36) (and substantially parallel to the forehead of a patient). The plane A is farther away from the patient (forehead of a patient) than plane B. The attachment points of the harness lie in the planes A and B. The attachment points of the harness are therefore in a different plane than the attachment points of the strap coupling (23) of the forehead support in the case of the clips.

Figure 5:
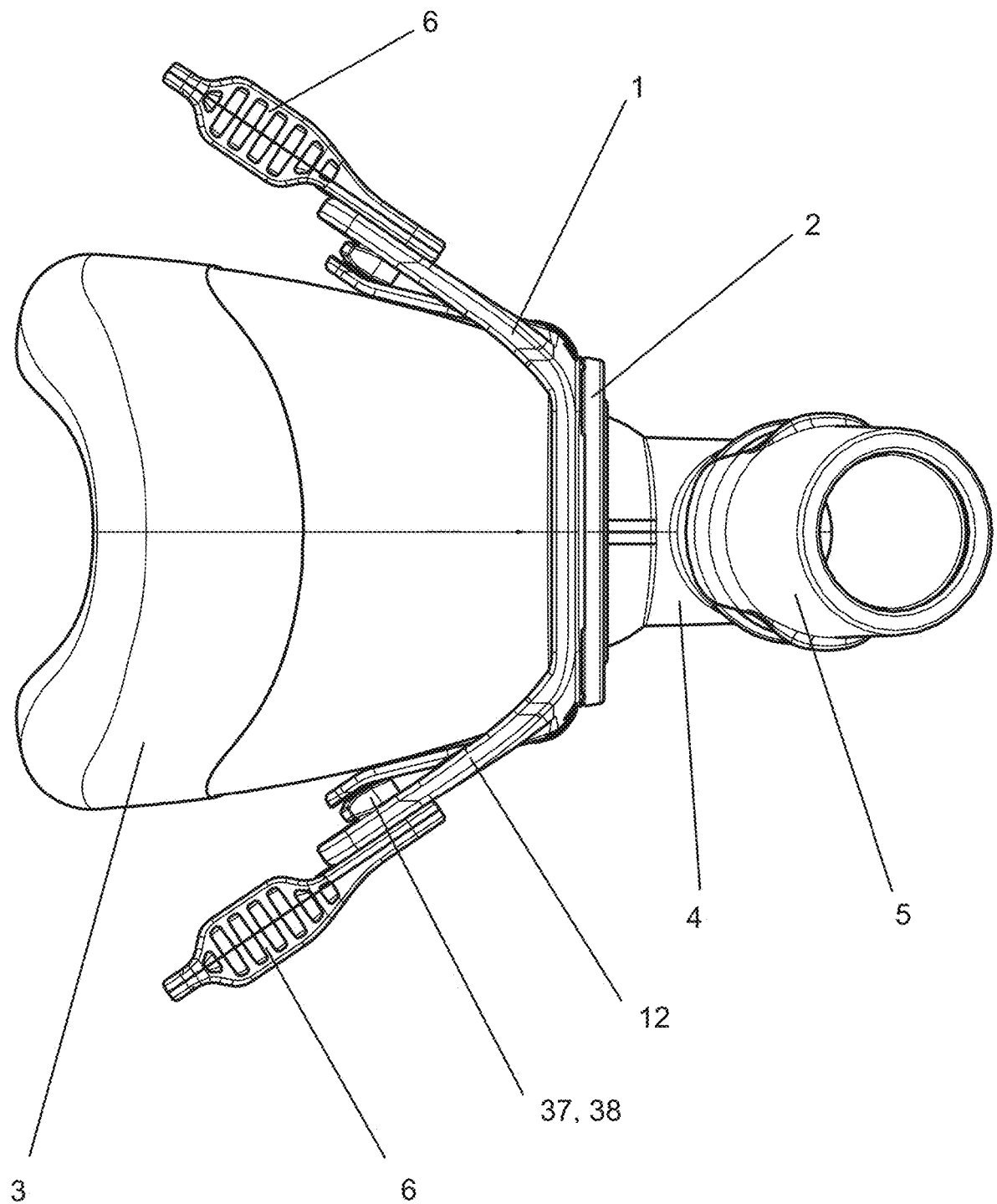
FIG. 5 shows a bottom view of the respiratory mask shown in FIG. 1.

FIG. 5 shows a bottom view of the respiratory mask shown in FIG. 1. It reveals the mask body (1), the forehead support (2), the mask bead (3) on the side directed toward a patient, the attachment piece (4) with mounted sleeve (5) on the side directed away from a patient, and clips (6) for coupling a strap to the respiratory mask.

Figure 6:
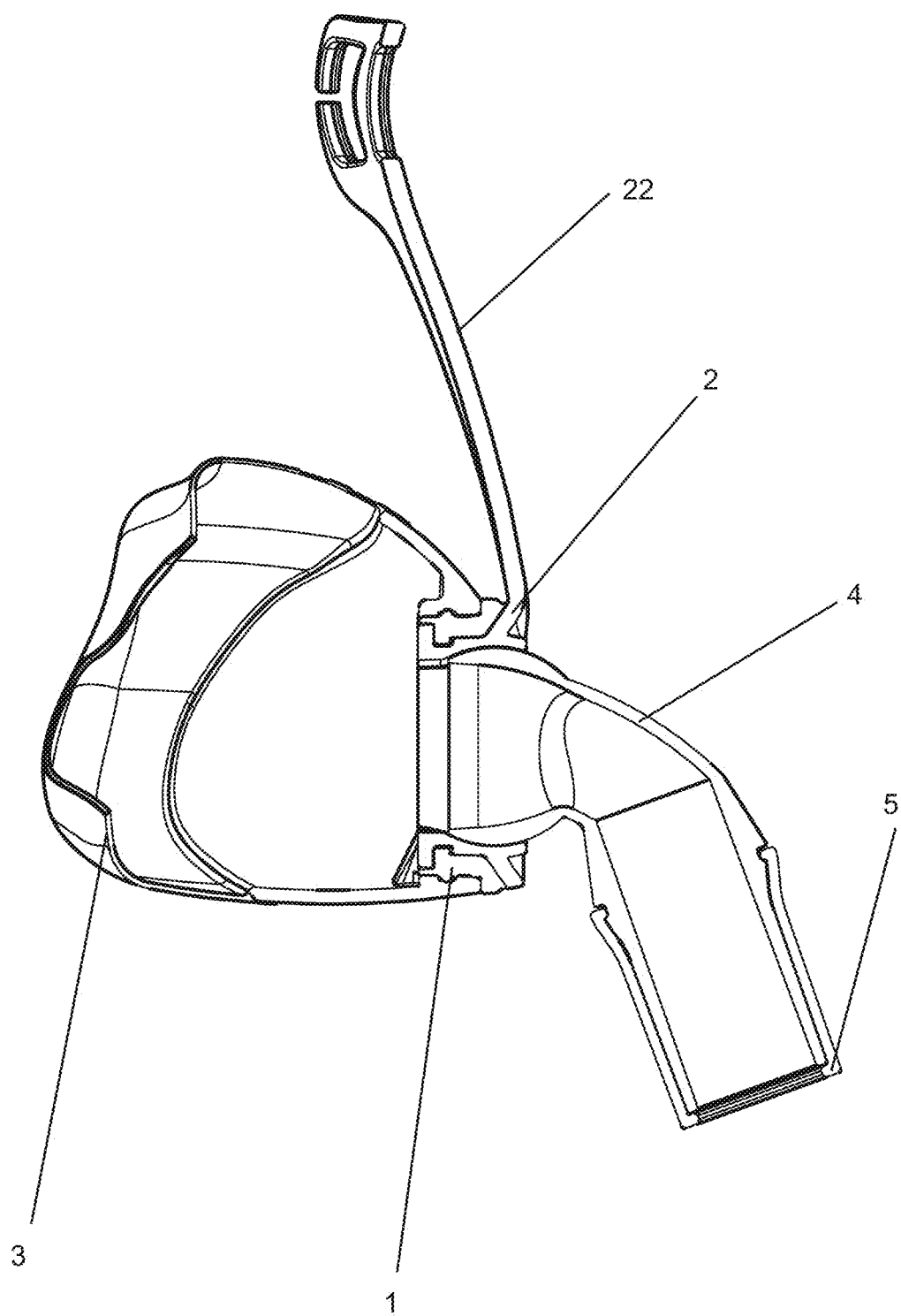
FIG. 6 shows a vertical section of the respiratory mask shown in FIG. 1.

FIG. 6 shows a vertical section through the center of the respiratory mask shown in FIG. 1. It reveals the mask body (1), the forehead support (2), the mask bead (3) on the side directed toward a patient, and the attachment piece (4) with mounted sleeve (5) on the side directed away from a patient.

Figure 7:
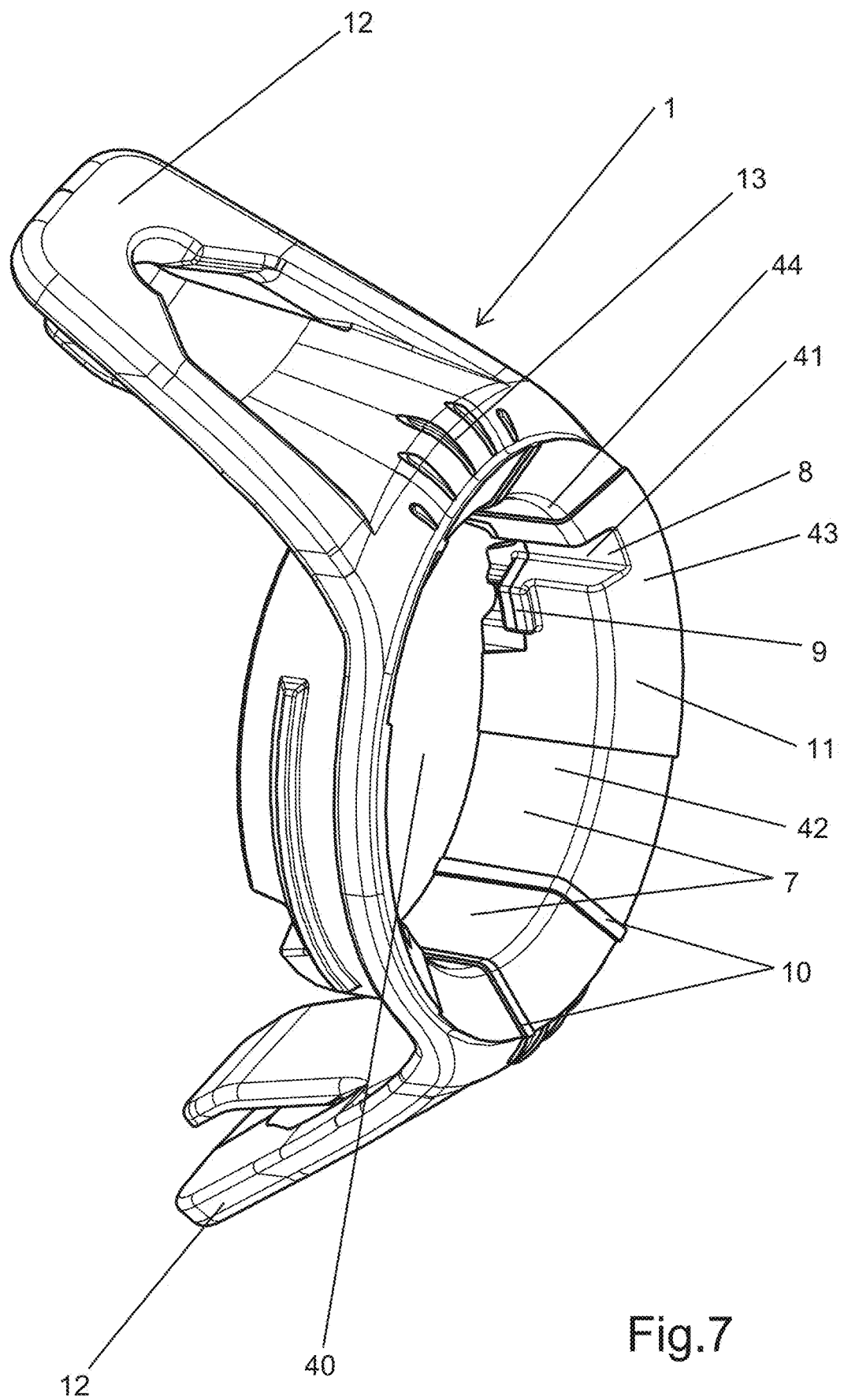
FIG. 7 shows a front perspective view of an embodiment, according to the invention, of a mask body.

FIG. 7 shows a perspective view of the mask body (1). Several outflow surfaces (7) can be seen on the inner surface of the mask body (1). The inner surface of the mask body (1) opens forwards in a funnel shape, whereas its basic shape in the rear region facing a patient is defined by a tube of constant diameter. In the inner contour of the mask body (1) there are at least two channels (8), which are each realized as a cutout in the tubular region and which extend into the funnel-shaped region. These channels (8) act in a dual function both as seats for the mechanical coupling of the forehead support (2), which coupling can be configured for example as a bayonet catch, and also as discharge channels for exhaled respiratory gases, the complete contour of which discharge channels is defined jointly by mask body (1) and forehead support (2). For the bayonet catch, a tooth (9) is provided in the rear region alongside each channel (8), which tooth (9) protrudes radially inward from the inner contour of the mask body (1) and affords the necessary mechanical resistance for the catch. Furthermore, several spacer ribs (10) are arranged on the inner surface of the mask body (1) and permit a connection of mask body (1) and forehead support (2) without play and/or with pretensioning. In the region (11) of the discharge channels (8), the material in the ring and funnel region (42, 43) is strengthened according to the height of the spacer ribs (10). Moreover, the spacer ribs (10) and the strengthened regions (11) laterally delimit the outflow surfaces (7).

Additional cutouts in the funnel-shaped region of the inner surface of the mask body (1) are also conceivable in order to form one or more additional outflow channels.

At its sides, the mask body (1) has two wings (12), which each have a mechanical structure for receiving a strap coupling. The strap coupling can be provided, for example, by a clip (6). In the front region of the mask body (1), the latter is provided with knobs (13) at the level of the wings (12), which knobs (13) permit a better grip during the handling of the respiratory mask.

Figure 8:
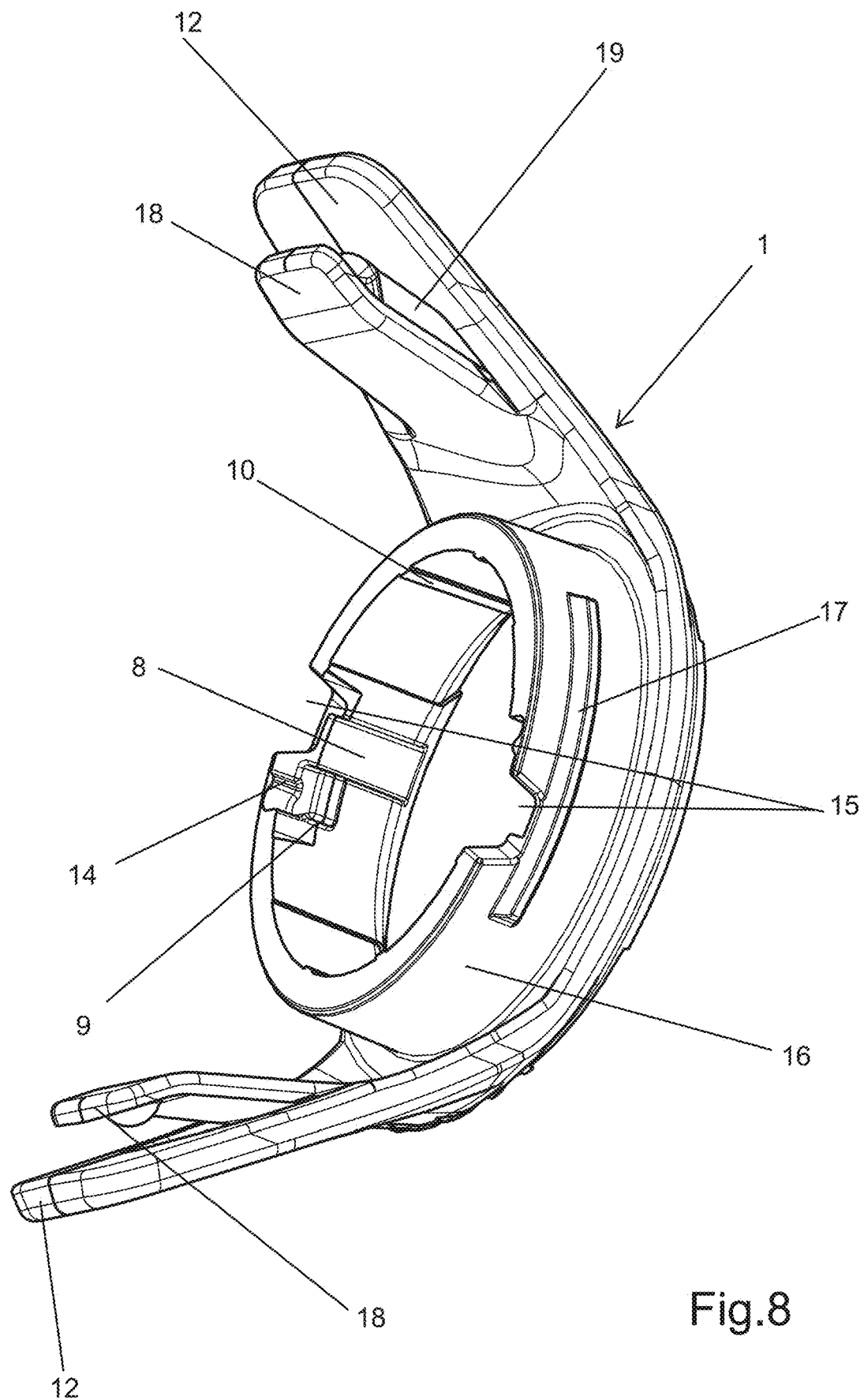
FIG. 8 shows a rear perspective view of the mask body shown in FIG. 7.

FIG. 8 shows a perspective view of the mask body (1) from the rear. This view reveals a configuration of the structure that is arranged in the mask body (1) for the bayonet catch. The channel (8) is supplemented in its basic shape behind the tooth (9) to form an L-shaped cutout, which permits the typical plug and screw connection. In the contour region behind the tooth (9), a locking tooth (14) is provided which secures the connection.

In the embodiment of the respiratory mask shown in FIG. 8, a mechanical coding (15) is additionally realized in the mask body (1) in such a way that the mask bead (3) can be connected to the mask body (1) only in intended positions. This connection is effected by plugging the mask bead (3) onto the outer contour (16) of the mask body (1). In the embodiment shown, the connection is secured by at least one undercut (17) on the outer contour (16) of the mask body (1). Besides the circular outer contour (16) illustrated, other configurations are also conceivable. In particular, an oval shape of the outer contour (16) is conceivable. In combination with the shape of the connection opening of the mask bead (3), which connection opening can also be shaped differently with an inner circumference smaller than or equal to the outer contour (16) of the mask body (1), the stiffness and the ratio of height and width of the mask bead (3) can be adjusted. In particular, a combination of an oval configuration of the outer contour (16) and a circular configuration of the connection opening of the mask bead (3) is conceivable.

Besides the illustrated connection of mask bead (3) and mask body (1) by an undercut (17), other options are also conceivable. For example, bonding of the modules with the aid of a two-component adhesive is also possible.

The mechanical receiving structure provided in the region of the wings (12), and serving for a strap coupling, consists principally of a spring plate (18) in combination with a cutout (19) in the structure of the wing (12). The cutout (19) in this case is funnel-shaped. The cutout (19) can have a first portion with a moderate funnel shape (19a) and a second portion with a pronounced funnel shape (19b). The cutout (19) opens out in a locking region (39) which is adapted at least in part to the shape of the clip (6, 37, 38). The mask body additionally has guide structures (13) which direct the patient to the cutout (19) or the joining direction of the clips. Alternatively, the guide structures (13) can also be configured as mechanical structures (grooves, channels, edges or the like) which guide the clip in the direction of the cut-out.

Figure 9:
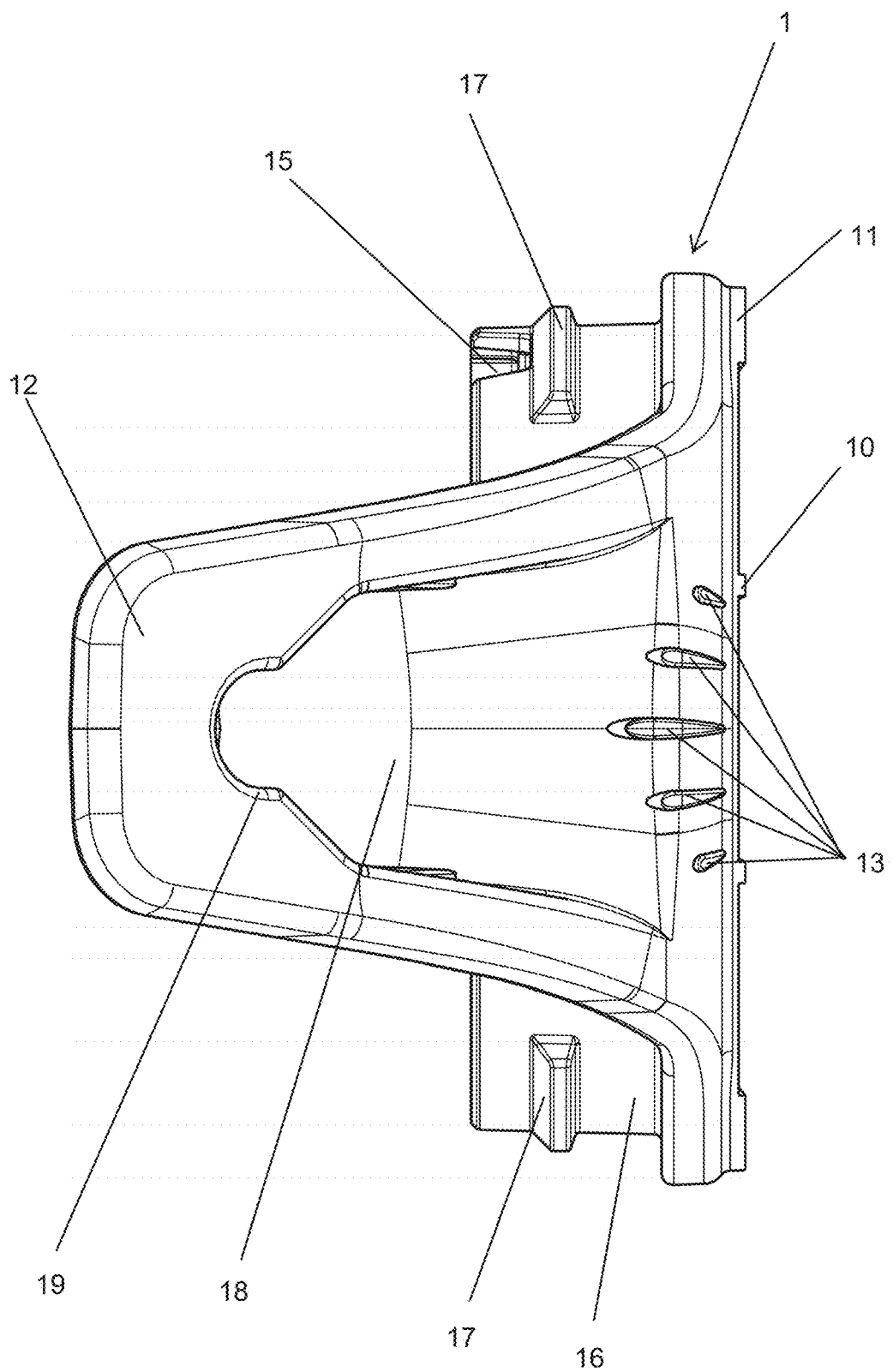
FIG. 9 shows a side view of the mask body from FIG. 7.

FIG. 9 shows a side view of the mask body (1). It reveals a funnel-shaped embodiment of the cutout (19) in the wing (12), which permits user-friendly insertion of the strap coupling, for example in the form of a harness clip (6). This is necessary, since this region is not located in the field of view of the patient during the use or fitting of the respiratory mask. The funnel (19) leads the clip (6) automatically to the locking point, in which the clip (6) is fixed by the spring plate (18).

Figure 10:
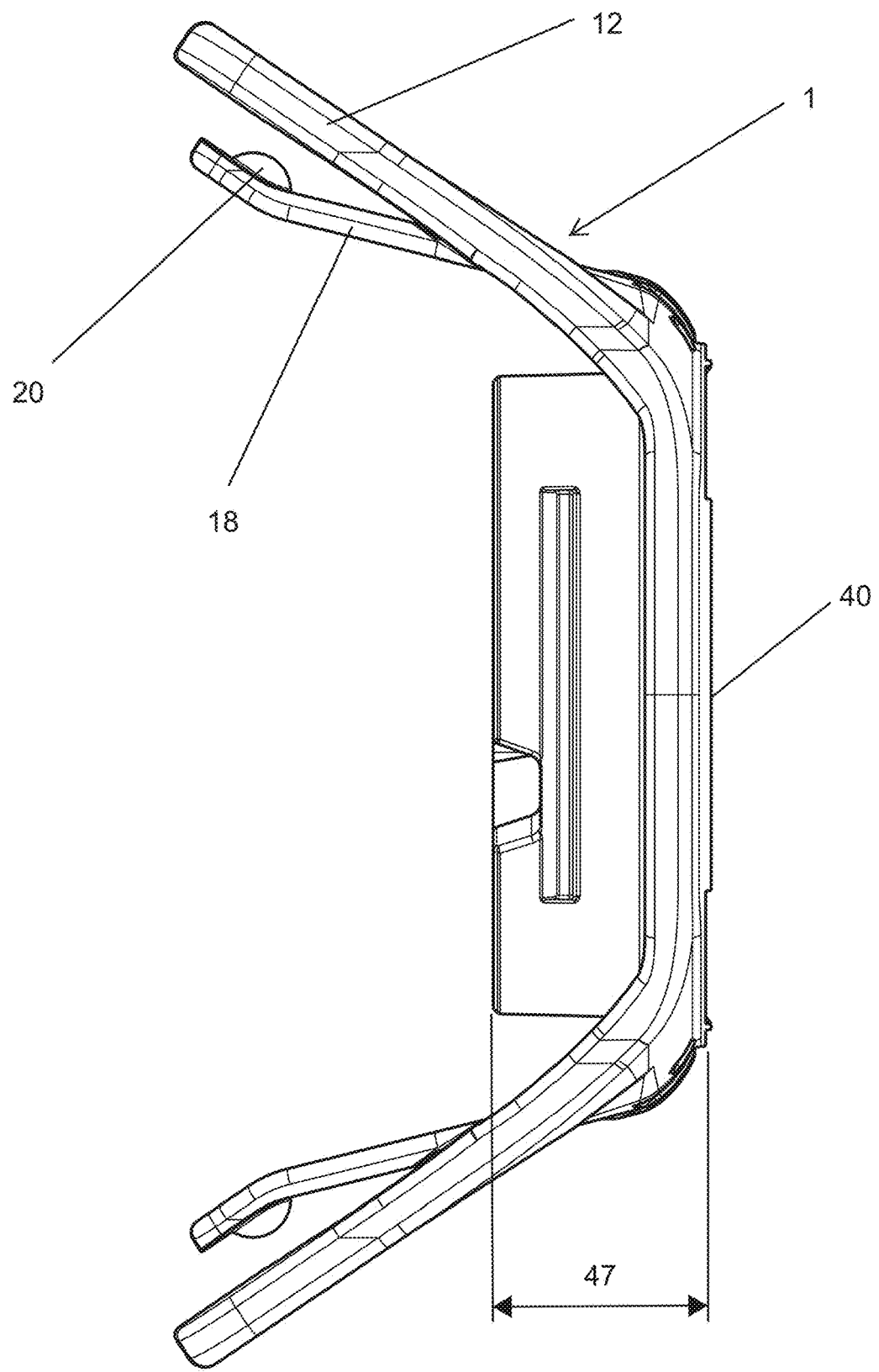
FIG. 10 shows a top view of the mask body from FIG. 7.

FIG. 10 shows an embodiment of the mask body (1) according to the invention from below. It reveals a locking stub (20) on the side of the spring plate (18) directed toward the wing (12), which locking stub (20) facilitates the locking engagement of the harness clip (6).

Figure 11:
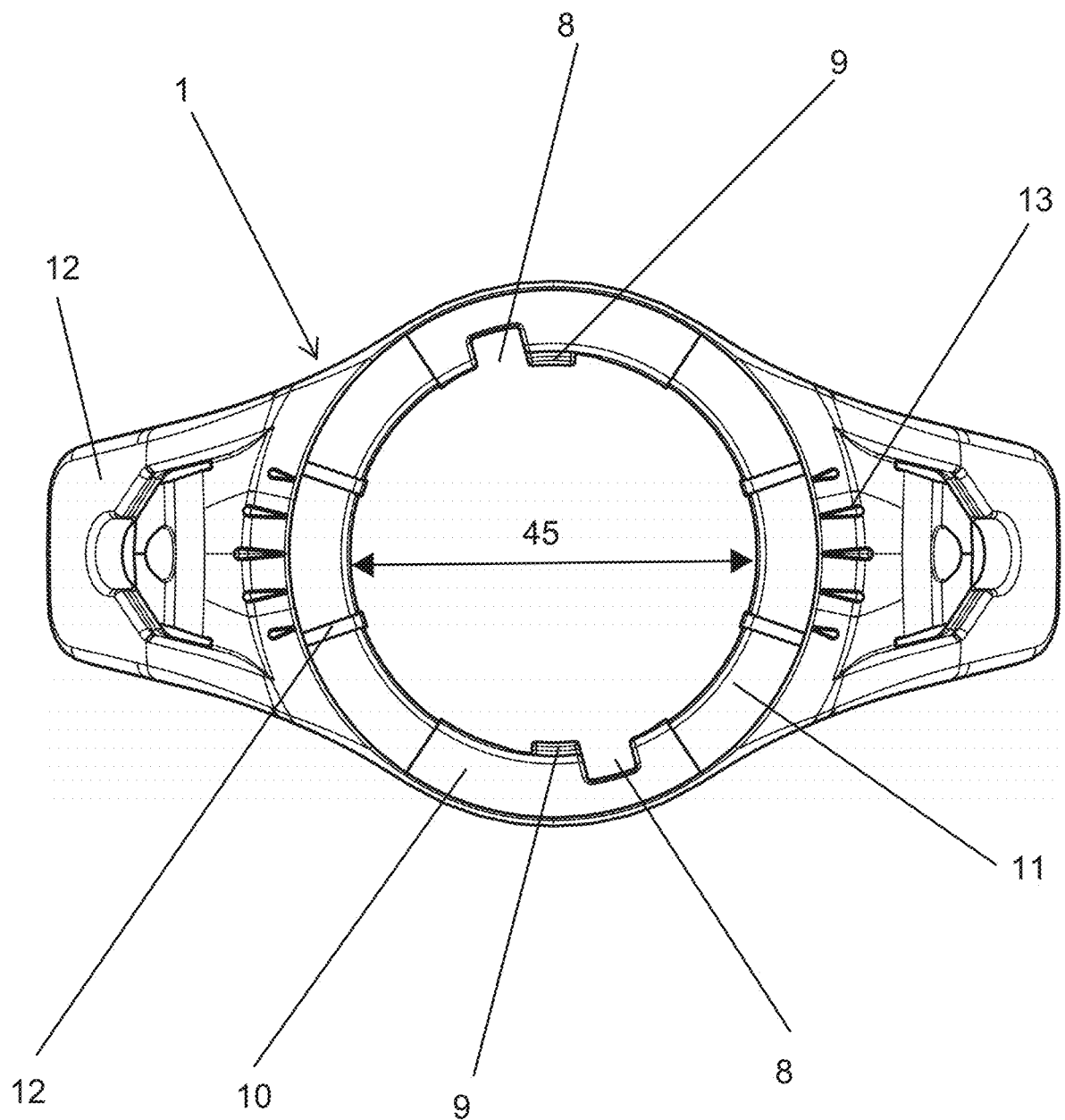
FIG. 11 shows a front view of the mask body from FIG. 7.

FIG. 11 shows a front view of the mask body (1) shown in FIG. 7. It reveals the rotational symmetry through 180° about an axis located at the center point of the inner radius and protruding perpendicularly from the drawing plane.

Figure 12:
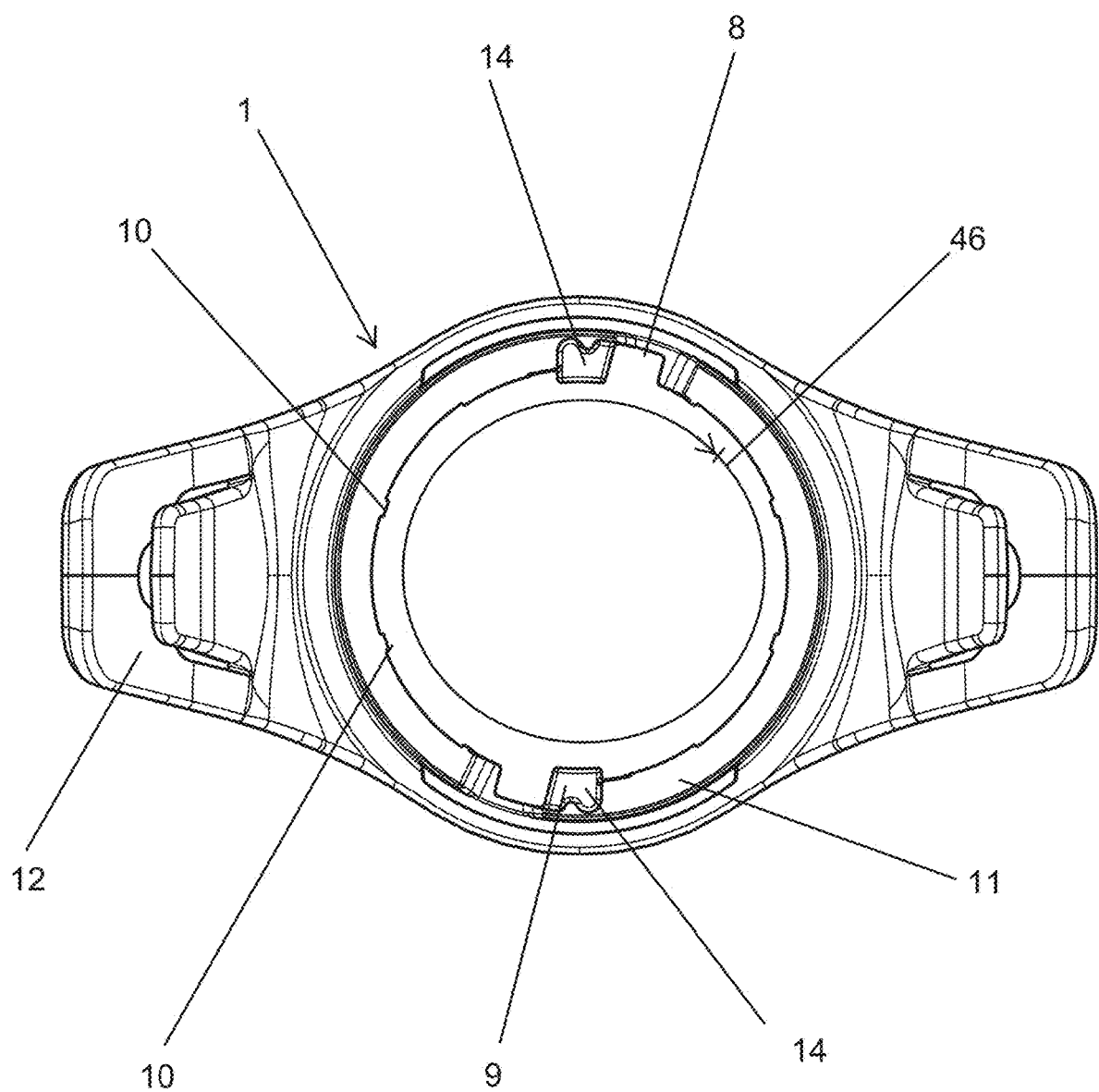
FIG. 12 shows a rear view of the mask body from FIG. 7.

FIG. 12 shows a rear view of the mask body (1) shown in FIG. 7. It reveals the spacer ribs (10) protruding radially from the inner contour (7), and the strengthened regions (11) about the outflow channels (8). The shape of the locking tooth (14) for the bayonet catch can also be seen, by means of which locking tooth (14) the bayonet connection, produced by the engagement with the mating piece on the forehead support (2), is secured against unwanted rotation and release.

Figure 13:
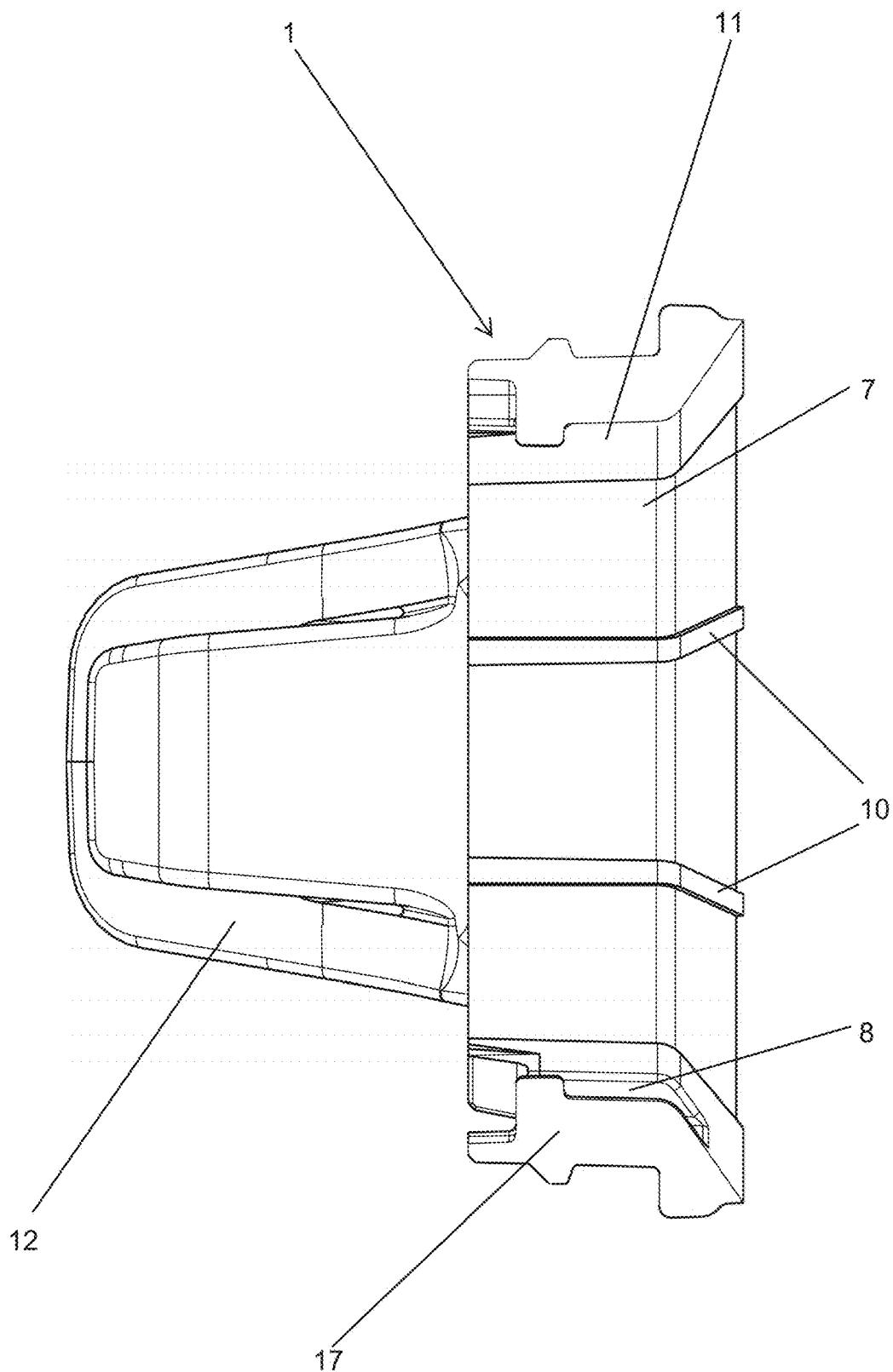
FIG. 13 shows a vertical section through the mask body from FIG. 7.

FIG. 13 shows a vertical section through the center of the mask body (1) shown in FIG. 7. The funnel-shaped opening of the inner contour of the mask body (1) to the right-hand side can be seen. In the region of the inner surface of the mask body (1) lying between the strengthened regions (11) about the outflow channels (8), two spacer ribs (10) are in each case arranged at equal distances from each other and from the strengthened regions (11). The number and positioning of the spacer ribs (10) can vary in embodiments of the respiratory mask according to the invention.

Figure 14:
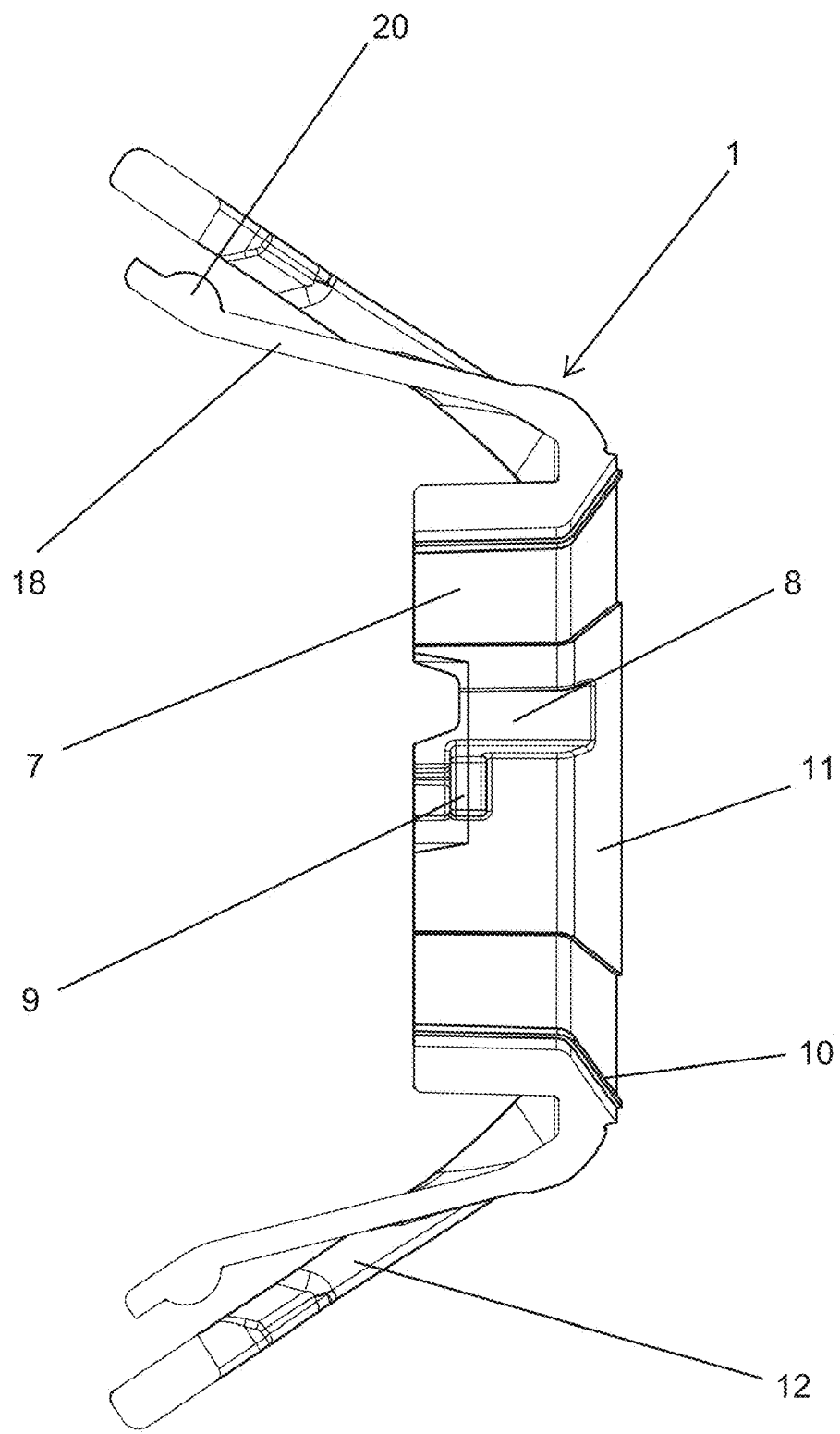
FIG. 14 shows a horizontal section through the mask body from FIG. 7.

FIG. 14 shows a horizontal section through the center of the mask body (1) shown in FIG. 7. It reveals the positioning of spring plate (18) with locking stub (20) relative to the main body of the wing (12). The distance between the spring plate (18) and the main body of the wing (12) is adapted to a clip (6).

Figure 15:
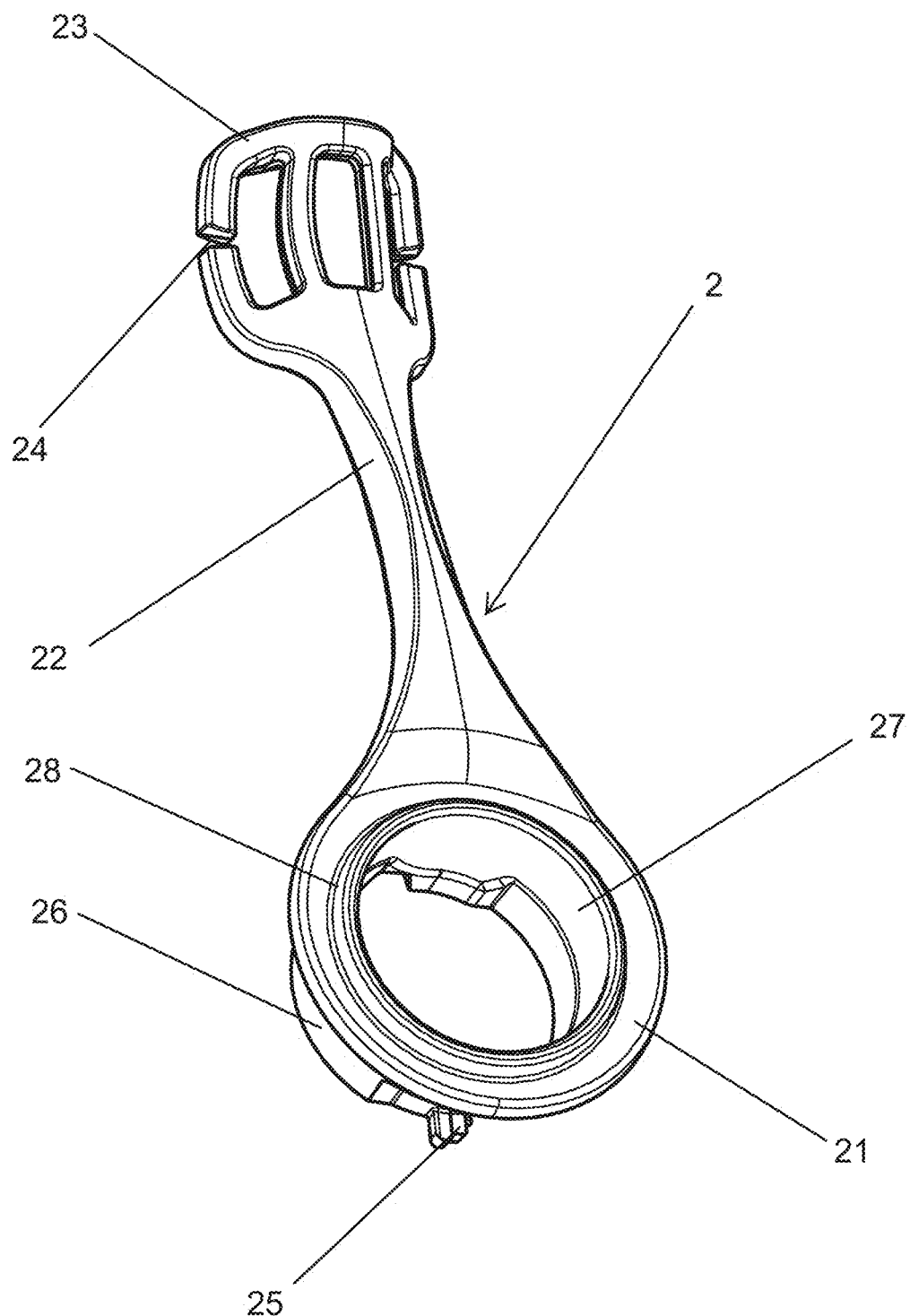
FIG. 15 shows a front perspective view of an embodiment of the forehead support according to the invention.

FIG. 15 shows an embodiment of a forehead support (2) according to the invention. The base of the forehead support (2) is formed by the forehead support connector (21), with which the forehead support (2) is secured to the mask body (1). A web (22) connects the forehead support connector (21) to the strap coupling (23) at the head of the forehead support (2). The strap coupling (23) is composed of three cutouts in the structure of the forehead support (2), said cutouts being arranged horizontally alongside one another and extending longitudinally in a vertical direction. The two outer cutouts each have an additional gap (24) in the outwardly directed structure of the forehead support (2). These gaps (24) can be used for engaging the holding straps, at the forehead height of a patient, into the strap coupling (23). Alternatively, the strap can also be guided through the centrally positioned cutout.

Other embodiments of the strap coupling (23) are also conceivable. For example, it can also be realized by only two cutouts with an additional gap (24).

In the embodiment shown, the web (22) is significantly reduced in width compared to the head part with strap coupling (23) and to the forehead support connector (21). This permits an attractive, slim design and saves on material.

To complete the bayonet catch provided in the mask body (1), the forehead support connector (21) offers a number of closure teeth (25) corresponding in position and number to the channels (8) present in the mask body. These closure teeth (25) protrude radially outward from the outer contour of the connection ring (26) and in turn each have a further radially outwardly directed tooth which, together with the locking tooth (14) in the mask body (1), ensures that mask body (1) and forehead support (2) are locked in the intended position. The inner contour of the forehead support connector (21) is configured as a ball cage (27), which can movably bear the attachment piece (4). Toward the attachment piece (4), the ball cage (27) is delimited by an outwardly narrowing ring structure (28).

Figure 16:
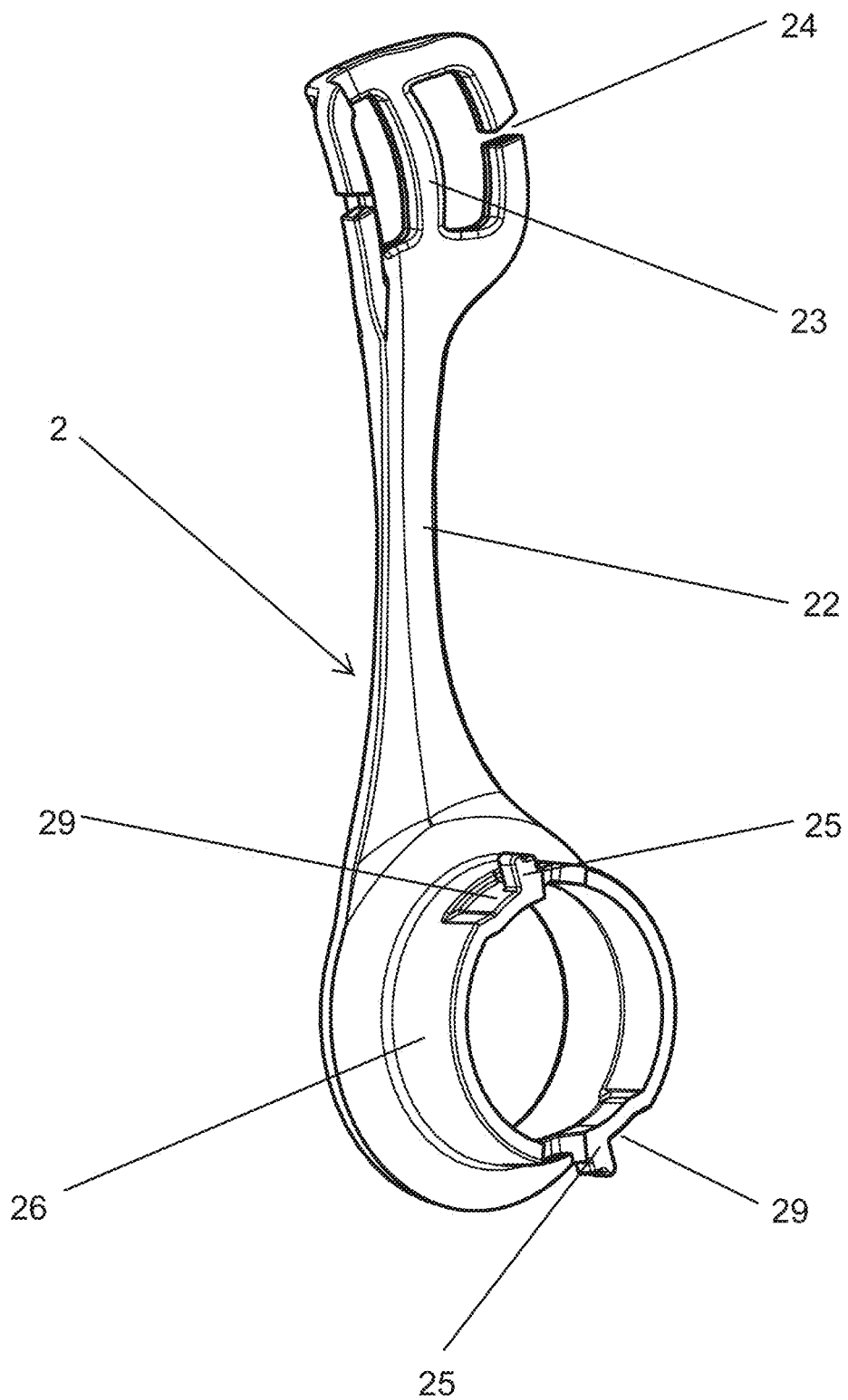
FIG. 16 shows a rear perspective view of a forehead support from FIG. 15.

FIG. 16 shows a perspective view of a forehead support (2) from the rear. The illustrated forehead support (2) has tow closure teeth (25). However, a larger number of closure teeth (25) matching the respective mask body (1) is also conceivable. Cutouts (29) can be seen in the outer contour of the connection ring (26) alongside the closure teeth (25). These cut-outs (29) serve as additional outflow channels and lead the exhaled gases around the respective closure tooth (25) to the corresponding channel (8) arranged in the mask body (1). It is additionally conceivable for such a cutout (29) also to be used as a mechanical coding for a defined orientation of mask body (1), forehead support (2) and mask bead (3). For this, the structure of the mask body (1) must be suitably permeable in the region of its mechanical coding (15).

Figure 17:
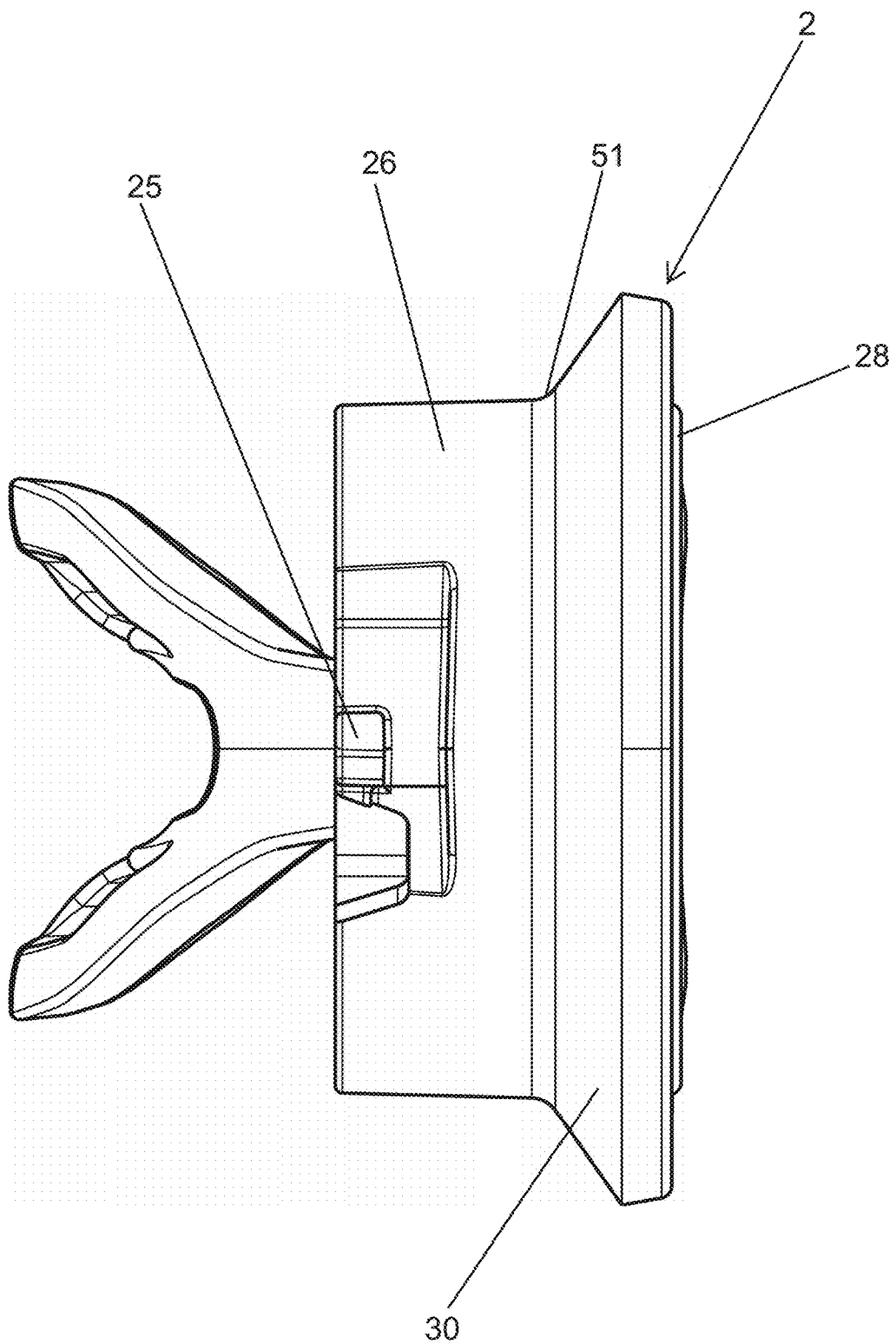
FIG. 17 shows a bottom view of the forehead support from FIG. 15.

FIG. 17 shows a bottom view of the forehead support (2) from FIG. 15. It reveals the outer contour of the forehead support connector (21), which is adapted to the inner contour of the mask body (1) and which is likewise composed of a ring and a funnel. This contour forms the discharge surface (30) on the forehead support side and, together with the inner surface of the mask body (1), defines the shape of the discharge channels and the exhalation gaps.

Figure 18:
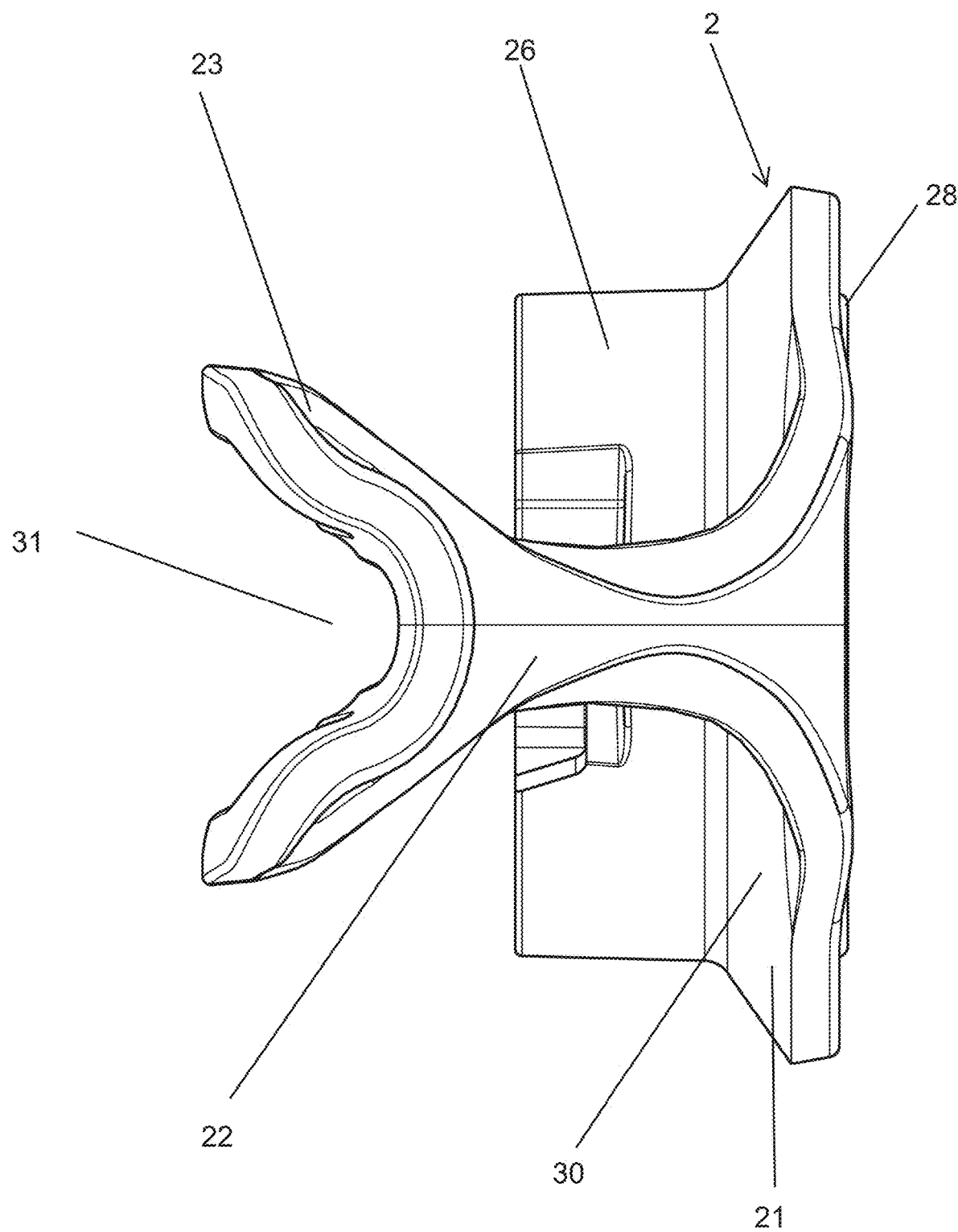
FIG. 18 shows a top view of the forehead support from FIG. 15.

FIG. 18 shows a top view of the forehead support (2) from FIG. 15. It reveals that the head part of the forehead support (2) protrudes toward a patient in relation to the forehead support connector (21). The shape of the head of the forehead support (2) accommodating the strap coupling (23) has a recess (31) which, between the forehead of a patient and the strap coupling (23) in the forehead support (2), affords a space in which the straps can lie.

The shape of the head of the forehead support (2) accommodating the strap coupling (23) has a recess (31) which affords a space between the forehead of a patient and the strap coupling (23) in the forehead support (2). In a view from above, the recess (31) has a Y shape together with the structural elements of the harness coupling. The contour in the region of the recess (31) has a rounded profile with one or more radii. In accordance with the material of the harness coupling and the wall thicknesses, the Y-shaped structure can offer an elasticity that permits adaptation of the head part of the forehead support (13) relative to the forehead of the patient.

The strap coupling (23) has a plane of symmetry S and at least four receiving means (41, 42) for a harness end of a harness, wherein the receiving means are arranged in pairs on both sides of the plane of symmetry S, and a harness end can be secured alternatively on the first receiving means (41) or on the second receiving means (42) on one side of the coupling element. The receiving means 41 is spatially adjacent to the receiving means 42 and arranged closer to the plane of symmetry S than the receiving means 42.

Figure 19:
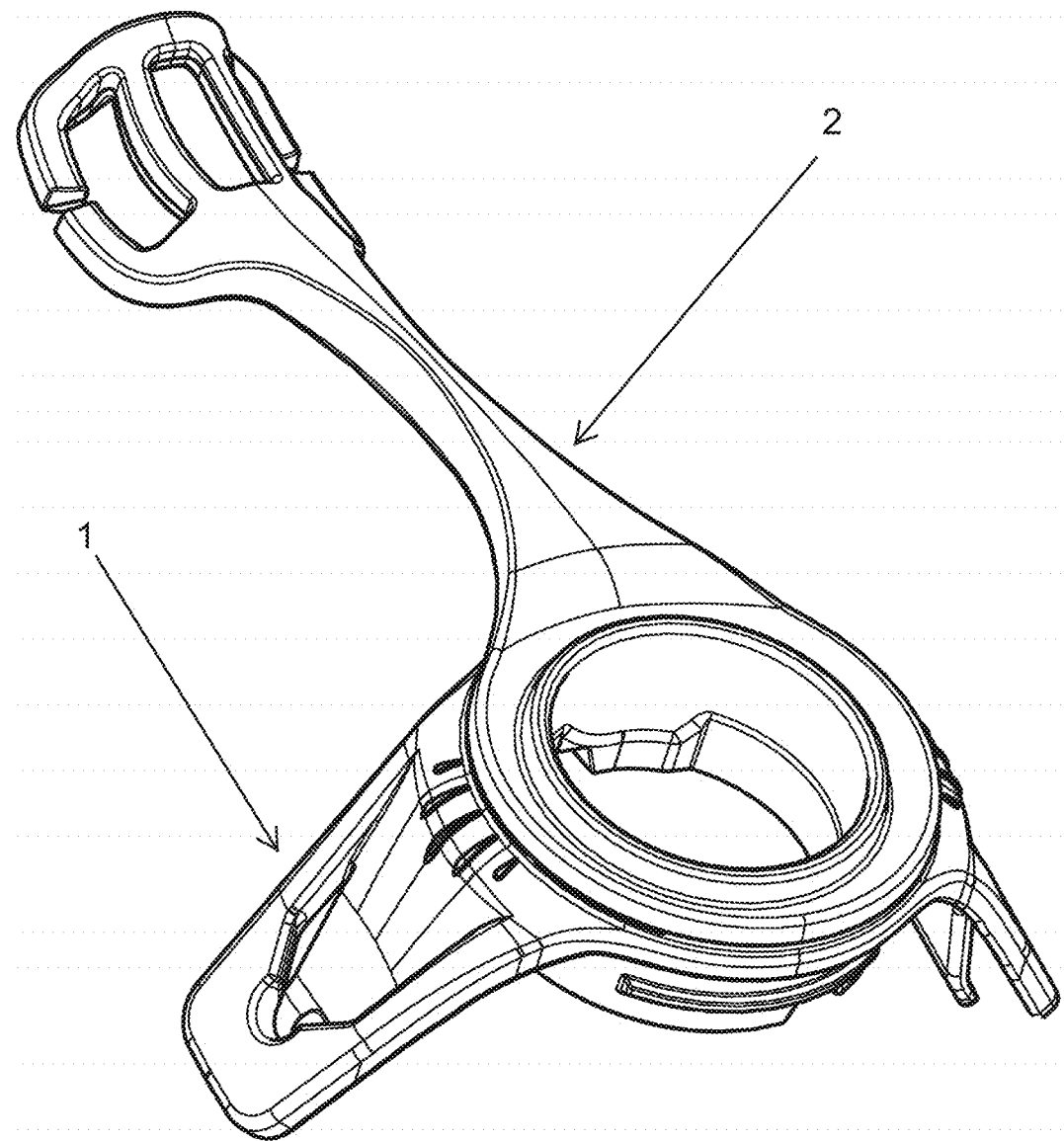
FIG. 19 shows a perspective view of a module of a breathing device according to the invention, consisting of mask body and forehead support.

FIG. 19 shows a perspective view of mask body (1) and forehead support (2) as an assembled module. In a rotationally symmetrical configuration of the mask body (1), the latter can be connected to the forehead support (2) in precisely two positions which are offset by 180° and which are functionally identical. It is thereby possible to achieve a simplification of the assembly of the modules of the respiratory mask.

Figure 20:
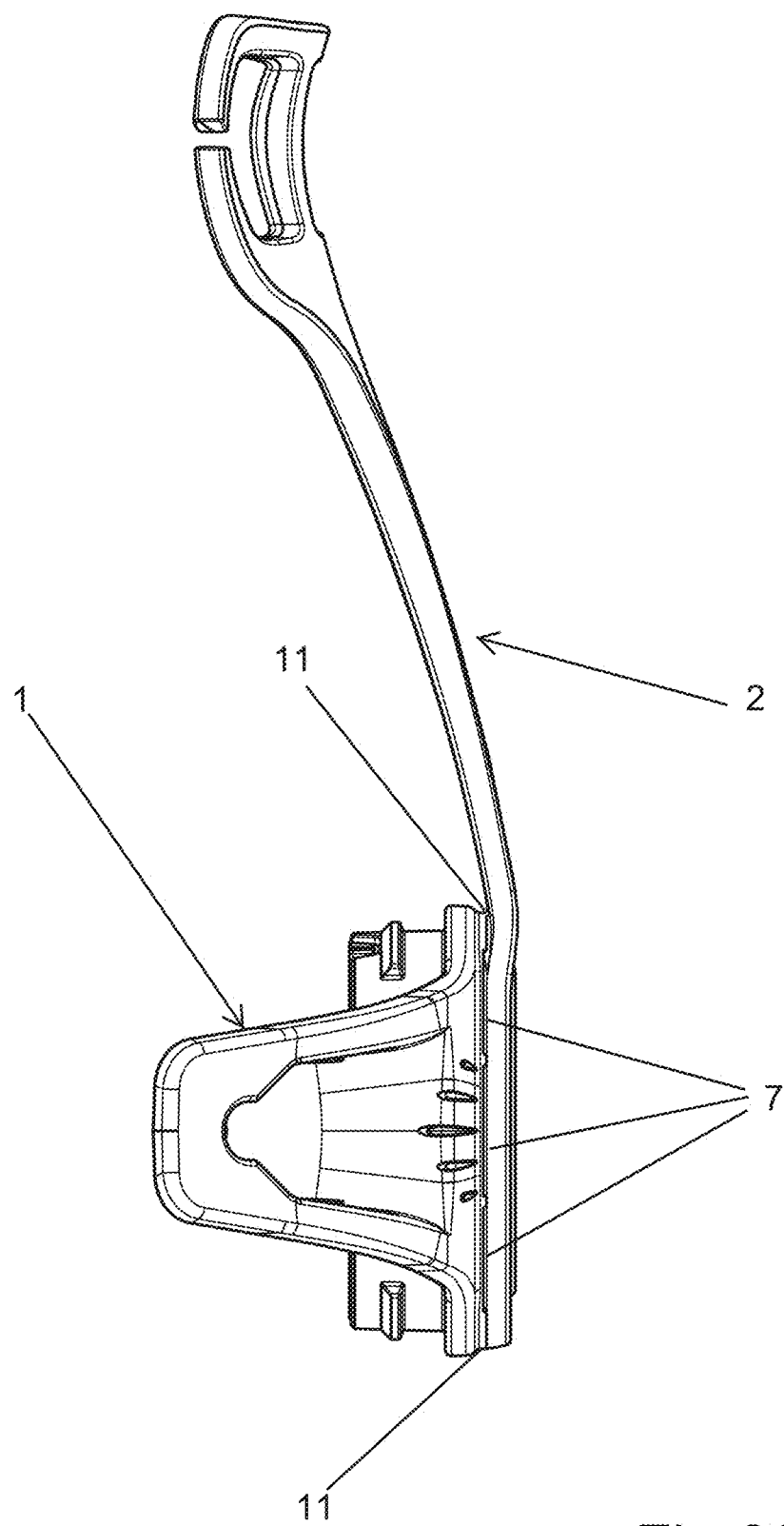
FIG. 20 shows a side view of the module shown in FIG. 19.

FIG. 20 shows a side view of the assembled module of mask body (1) and forehead support (2). The gaps remaining between the discharge surfaces (7) of the mask body (1) and between the outflow channels (8) and the discharge surface (30) of the forehead support connector (21) serve as a guide structure for the exhaled air. By means of the elevated structure in the region (11) of the channels (8) in the mask body (1), sealing of the exhalation gap in a defined region is achieved at the upper side in the direction of the forehead support (2). This serves to avoid air being discharged into regions where it is uncomfortable for a patient, in particular the eyes.

Figure 21:
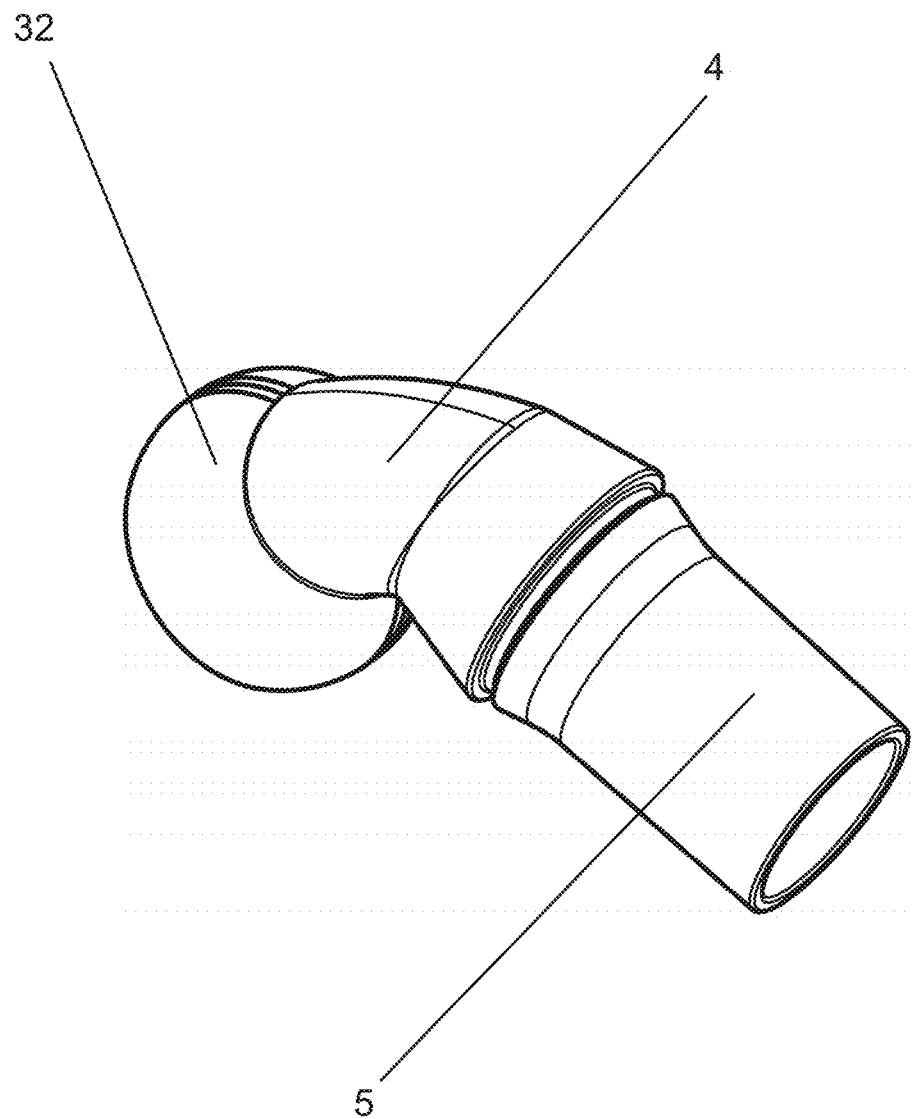
FIG. 21 shows a perspective view of an attachment piece according to the invention.

FIG. 21 shows a perspective view of an attachment piece (4) according to the invention. The attachment piece (4) is configured as an angled tube structure and has, at one end, a surface contour (32) that corresponds to a partial sphere. This partial sphere (32) serves for the movable connection of attachment piece (4) and forehead support (2) by means of the ball cage (27) formed in the forehead support connector (21).

At the other end, a rotatably mounted sleeve (5) is provided as attachment for a hose (not shown).

Figure 22:
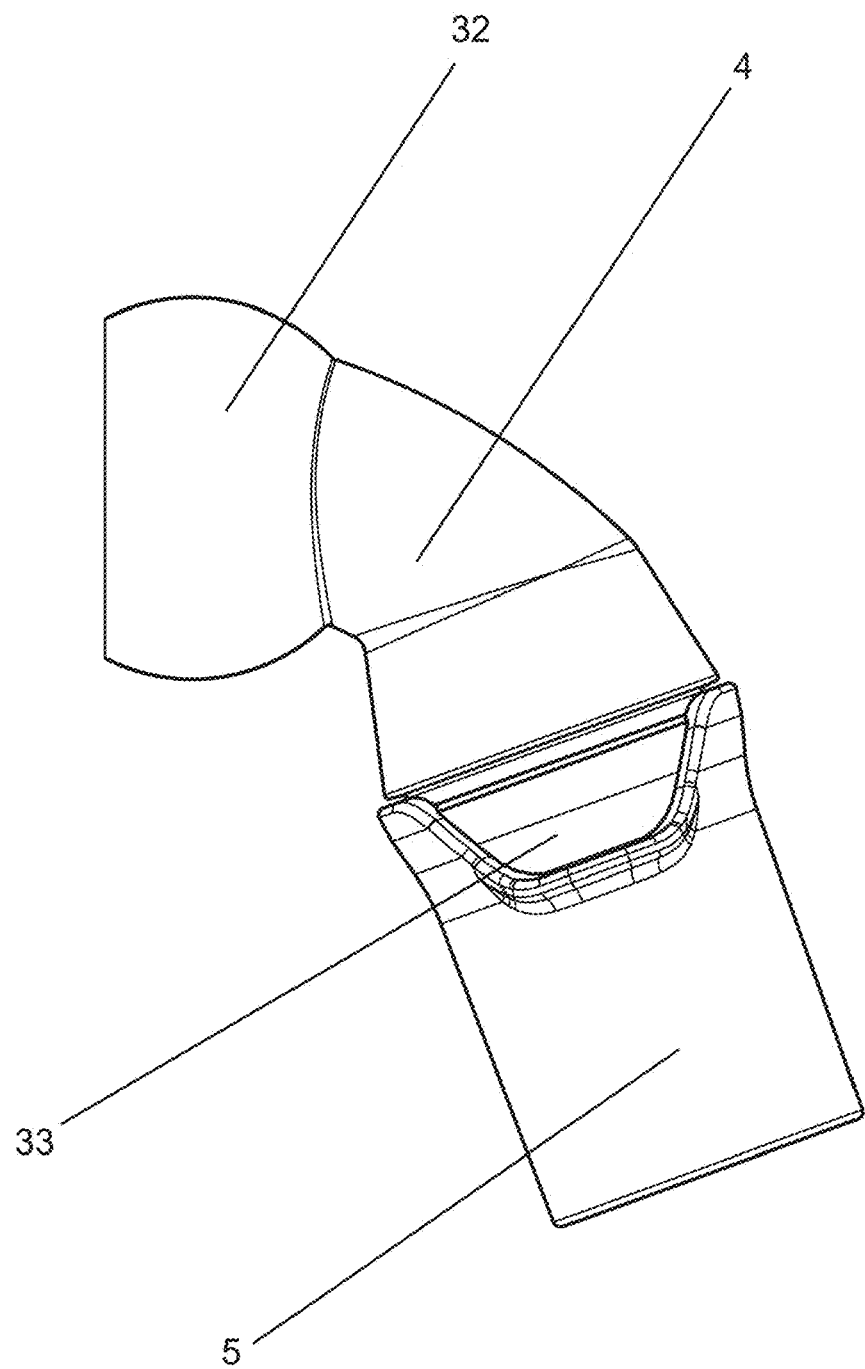
FIG. 22 shows a side view of an attachment piece according to the invention.

FIG. 22 shows a side view of an attachment piece (4) according to the invention with an alternative rotatably mounted sleeve (5). The sleeve (5) becomes thicker at the end oriented toward the respiratory mask and has cutouts (33) at this end.

Figure 23:
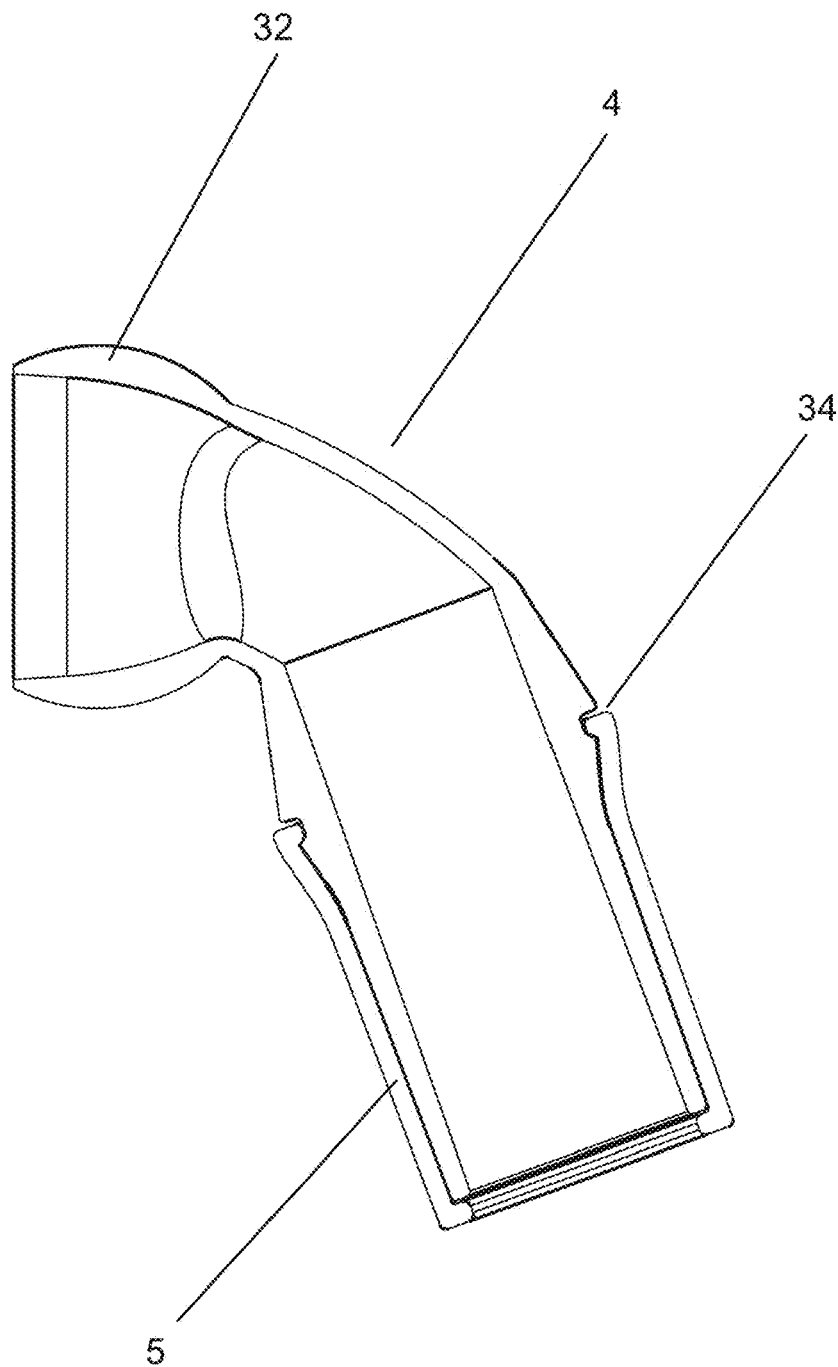
FIG. 23 shows a vertical section of the attachment piece from FIG. 21.

FIG. 23 shows a vertical section through the attachment piece (4). It reveals the surface contour in the shape of a partial sphere (32) at the upper end, the tubular inner structure, and a thickening of the structure toward an annularly extending groove (34), which rotatably supports the sleeve by means of an undercut present thereon.

Figure 24:
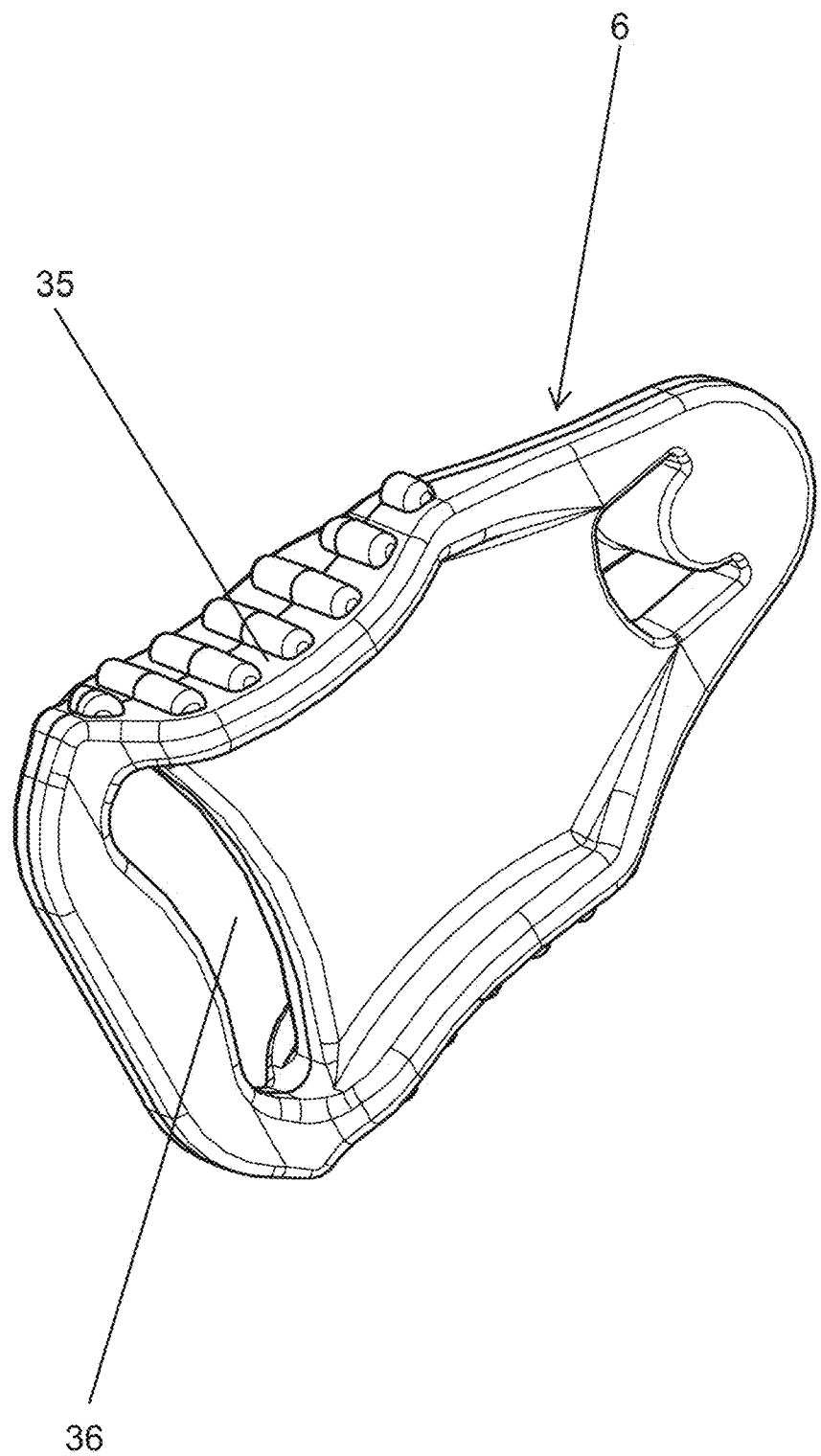
FIG. 24 shows a perspective view of a clip according to the invention for receiving a strap, and the connection to the mask body from the side directed away from the mask.

FIG. 24 shows a perspective view of a harness clip (6). On its top side and underside, the clip (6) has depressions which are occupied by knobs or ribs (35). The latter serve for an improved grip. At one end, the clip (6) has an eyelet (36) through which a retaining strap can be pulled and thus secured.

The clip has a round, mushroom-shaped undercut with a pin. The pin locks in the locking point (39).

The spring plate is supported on one side on the mask bead (3). When the clip (6) is inserted into the locking point, the spring plate is forced against the mask bead (3) and elastically deforms same. In the locking point, the bead, having returned resiliently to its original shape, secures the position of the spring plate, which is also returned resiliently to its original position. The spring plate holds the clip in the locking position in the locking point. The bead additionally secures the position of the spring plate.

The mobility of the clip relative to the mask body is possible only in one spatial plane because of the round, mushroom-shaped undercut on the clip and the fixing in the funnel. In this way, the clip is movable substantially in only one plane parallel to the wing or parallel to the bead. A mobility of the clip toward the face of the patient is possible only in a range of 1° to 10°, preferably 1° to 7°.

Figure 25:
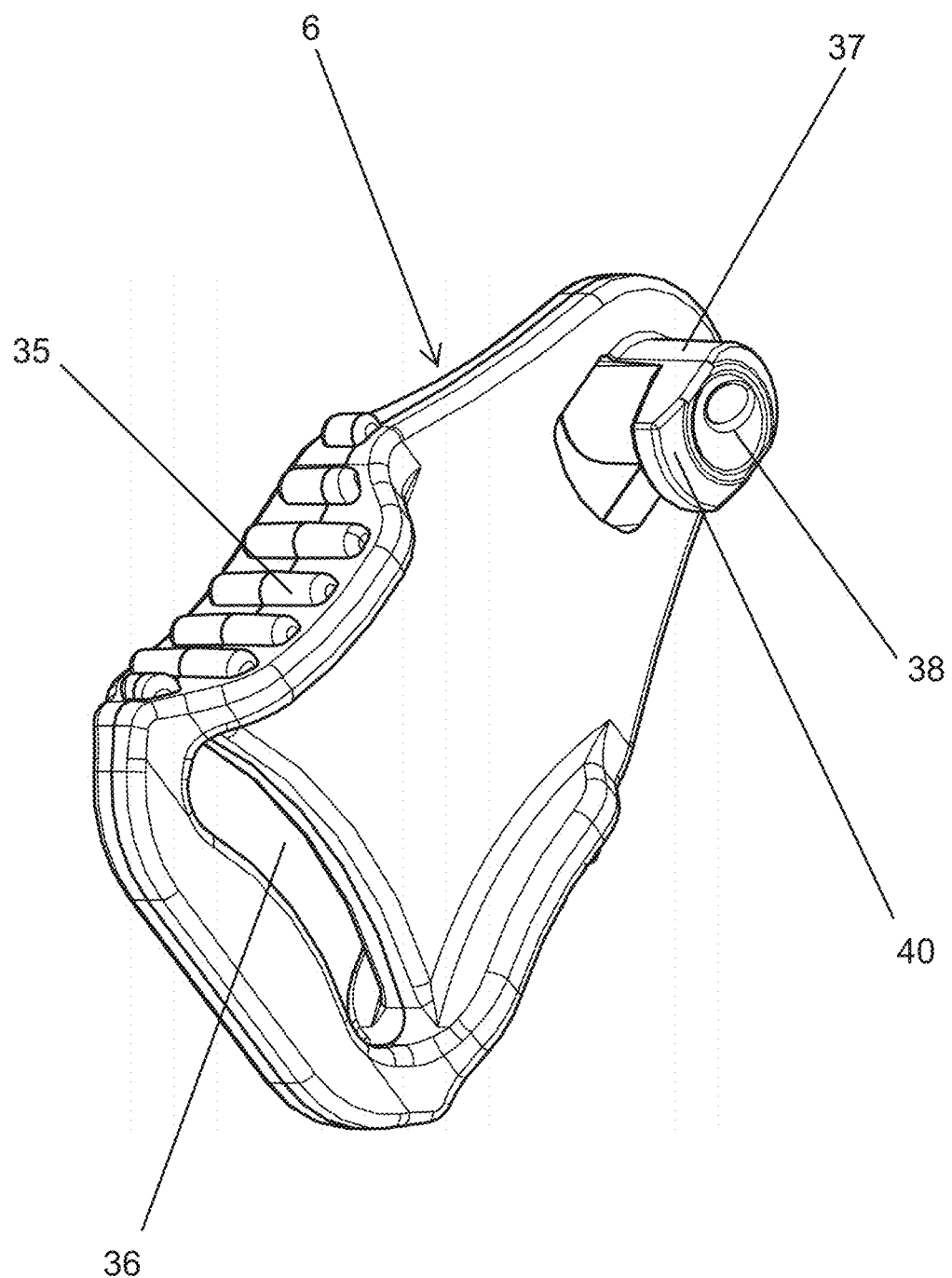
FIG. 25 shows a perspective view of the clip from FIG. 24, from the side directed toward the mask.

FIG. 25 shows a perspective view of the harness clip (6) from the side oriented toward the respiratory mask in the assembled state. It reveals a stub (37) with a mushroom-shaped undercut (40). The undercut (40) can be circumferentially round. The undercut (40) can also be formed only in subregions and for example be directed toward the opening (36). A depression (38) configured as a socket in the head of the stub (37) ensures, in cooperation with the locking stub (20) on the spring plate (18) of the mask body (1), that the harness clip (6) engages in the intended position on the wing (12) of the mask body (1). In the head of the pin (37), a locking pin (20) can also be formed which, with a depression (38) configured as a socket on the spring plate (18) of the mask body (1), ensures the locking engagement of the harness clip (6).

The depression (38)/the locking pin (20) can be axially centered in the axial direction of the pin (37). The clip is then pivotable vertically up and down about the axis of the pin (37).

The depression (38)/the locking pin (20) can also be axially uncentered in the axial direction of the pin (37). A pivoting movement of the clip about the axis of the pin (37) then leads to release of the connection between depression (38) and locking pin (20). The clip is then pivotable vertically up and down, but this movement in this case serves to release the clip from the locking position.

What is claimed is:

1. A respiratory mask, wherein the mask comprises a mask bead, which seals off the mask in a direction of a patient, a mask body, and at least one wing for receiving a harness clip for fixing a head harness on the mask, the wing having a funnel-shaped cutout, and the harness clip locking in a region of a locking point of the cutout.

2. The respiratory mask of claim 1, wherein the cutout has two regions which are funnel-shaped to different extents.

3. The respiratory mask of claim 1, wherein the locking point is arranged in the narrowest region of the funnel-shaped cutout.

4. The respiratory mask of claim 1, wherein the mask body comprises, in a region of the wing, a spring plate which is arranged adjacent to and/or inside the cutout.

5. The respiratory mask of claim 4, wherein the spring plate leans at least partially on the mask bead.

6. The respiratory mask of claim 4, wherein the mask comprises a locking pin on a side of the spring plate facing toward the wing, which locking pin permits a locking engagement of the harness clip.

7. The respiratory mask of claim 4, wherein a mechanical auxiliary structure for strap coupling is provided by a funnel-shaped structure in the mask body.

8. The respiratory mask of claim 1, wherein the mask body comprises guide structures which direct a patient to the cutout and to a joining direction of the clips.

9. The respiratory mask of claim 8, wherein the mask body comprises, in a region of the wing, a spring plate which is arranged adjacent to and/or inside the cutout and the guide structures are arranged on a base of the spring plate.

10. The respiratory mask of claim 1, wherein the mask body comprises, in a region of the wing, a spring plate which is arranged adjacent to and/or inside the cutout, and the funnel guides the clip automatically to the locking point, in which the clip is fixed by the spring plate.

11. The respiratory mask of claim 10, wherein the clip slides over the spring plate when it is guided to the locking point.

12. The respiratory mask of claim 1, wherein the mask further comprises a forehead support.

13. The respiratory mask of claim 12, wherein the forehead support, by virtue of its structure, has at least two options for coupling straps.

14. The respiratory mask of claim 1, wherein the mask further comprises two different mechanical auxiliary structures for coupling straps.

15. The respiratory mask of claim 1, wherein strap coupling is embodied by at least one clip.

16. The respiratory mask of claim 1, wherein the harness clip comprises, on its upper face and lower face, depressions or elevations which are occupied by knobs or ribs, and, at one end, comprises an eyelet through which a retaining strap can be pulled and thus secured.

17. The respiratory mask of claim 1, wherein the harness clip comprises a pin with a mushroom-shaped undercut.

18. The respiratory mask of claim 17, wherein the harness clip further comprises a depression, configured as a socket, in a head of the pin.

19. The respiratory mask of claim 18, wherein the depression, in interaction with a locking pin on a spring plate of the mask body, ensures a locking engagement of the harness clip in an intended position on the wing of the mask body.

* * * * *